US007119202B1

(12) United States Patent
Belleau et al.

(10) Patent No.: US 7,119,202 B1
(45) Date of Patent: Oct. 10, 2006

(54) SUBSTITUTED-1,3-OXATHIOLANES AND SUBSTITUTED-1,3-DIOXOLANES WITH ANTIVIRAL PROPERTIES

(75) Inventors: Bernard Belleau, deceased, late of Montreal (CA); by Pierrette Belleau, legal representative, Montreal (CA); Paul Nguyen Ba, La Prairie (CA)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/468,362

(22) Filed: Jun. 6, 1995

Related U.S. Application Data

(60) Division of application No. 08/306,830, filed on Sep. 15, 1994, now abandoned, which is a continuation of application No. 07/564,160, filed on Aug. 7, 1990, now abandoned, which is a continuation-in-part of application No. 07/308,101, filed on Feb. 8, 1989, now Pat. No. 5,047,407.

(30) Foreign Application Priority Data

Feb. 7, 1990   (HU) ................................. 39 45/90
Feb. 8, 1990   (EP) ................................ 90310335

(51) Int. Cl.
*C07D 411/04* (2006.01)
(52) U.S. Cl. .................................... 544/317; 514/274
(58) Field of Classification Search ............... 544/317; 514/274
See application file for complete search history.

(56) References Cited

U.S. PATENT DOCUMENTS

| 4,000,137 | A | 12/1976 | Dronch .......................... 260/252 |
|---|---|---|---|
| 4,336,381 | A | 6/1982 | Nagata ........................... 544/313 |
| 4,415,573 | A | 11/1983 | Ochi ............................... 424/251 |
| 5,039,667 | A | 8/1991 | Tyrrell ............................ 514/45 |
| 5,118,672 | A | 6/1992 | Schinazi ......................... 514/47 |
| 5,204,466 | A | 4/1993 | Liotta ............................ 544/317 |
| 5,210,085 | A | 5/1993 | Liotta ............................ 514/274 |
| 5,539,116 | A | 7/1996 | Liotta et al. ................... 544/317 |

FOREIGN PATENT DOCUMENTS

| EP | A-0 206 497 | 12/1986 |
|---|---|---|
| EP | B-0 212 409 | 3/1987 |
| EP | A-0 337 713 | 1/1989 |
| EP | A-0 349 242 | 1/1990 |
| EP | A-0 363 582 | 4/1990 |
| EP | A-0 382 526 | 8/1990 |
| GB | 2 063 257 | 6/1981 |
| GB | 2 230 266 | 10/1990 |
| JP | 0059171 | 5/1977 |
| JP | 0021178 | 2/1978 |
| JP | 0167685 | 12/1981 |
| JP | 0169689 | 12/1981 |
| RU | 1035023 | 8/1983 |
| WO | WO 88/08001 | 10/1988 |
| WO | WO 89/04662 | 6/1989 |
| WO | WO 90/12023 | 10/1990 |
| WO | WO 91/01326 | 2/1991 |
| WO | WO 91/11186 | 8/1991 |
| WO | WO 91/17159 | 11/1991 |

OTHER PUBLICATIONS

Decision in Patent Interference No. 103,906, 2001.
Decision in Patent Interference No. 104,333, 2001.
Decision in Patent Interference No. 104,396, 2001.
Decision in Patent Interference No. 104,523, 2003.
Decision in Patent Interference No. 104,524, 2003.
M. Baba et al., "Both 2',3'-Dideoxythymidine and Its 2',3'-Unsaturated Derivative (2',3'-Dideoxythymidinene) are Potent and Selective Inhibitors of Human Immunodeficiency Virus Replication in Vitro", *Biochem. Biophys. Res. Commun.*, 142, pp. 128-134 (1987).
J. Balzarini et al., "Potent and Selective Anti-HTLV-III/LAV Activity of 2',3'-Dideoxycytidinene, the 2',3'-Unsaturated Derivative of 2',3'-Dideoxycytidine", *Biochem. Biophys. Res. Commun.*, 140, pp. 735-742 (1986).
B. Belleau et al., "Design and Activity of a Novel Class of Nucleoside Analogs Effective Against HIV-1", *V Intl. Conf. on AIDS Abs.*, T.C.O.1, p. 515 (1989).
R. Carlisle et al., "Cellular Pharmacology of the Anti-HIV BCH-189 (2'-Deoxy-3'-thiacytidine) in Human Peripheral Blood Mononuclear Cells (PBMC)" *Am. Assoc. Cancer Res. Abs. (81st Annu. Mtg.)*, 2435, p. 410 (1990).
G. Gosselin et al., "Systematic Synthesis and Biological Evaluation of α- and β-D-Lyxofuranosyl Nucleosides of the Five Naturally Occurring Nucleic Acid Bases", *J. Med. Chem.*, 30, pp. 982-991 (1987).
E. Hallonquist & H. Hibbert, "Studies on Reactions Relating to Carbohydrates and Polysaccharides—XLIV. Synthesis of Isomeric Bicyclic Acetyl Ethers", *Canadian J. Res.*, 8, pp. 129-133 (1933).

(Continued)

*Primary Examiner*—Brenda Coleman
(74) *Attorney, Agent, or Firm*—Millen, White, Zelano, Branigan, P.C.

(57) ABSTRACT

Disclosed are compounds of the formula $$R_1OCH_2 \underset{Z}{\overset{O}{\underset{2\phantom{x}5}{\bigtriangleup}}} R_2 \qquad (I)$$

wherein $R_1$ is hydrogen or an acyl group having 1 to 16 carbon atoms;
$R_2$ is a purine or pyrimidine base or an analogue or derivative thereof;
Z is O, S, S=O or $SO_2$; and
pharmaceutically acceptable derivatives thereof.

Also described are processes for and intermediates of use in their preparation, pharmaceutical compositions containing these compounds, and the use of these compounds in the antiviral treatment of mammals.

1 Claim, No Drawings

OTHER PUBLICATIONS

P. Herdewijn et al., "3'-Substituted 2',3'-Dideoxynucleoside Analogues as Potential Anti-HIV (HTLV-III/LAV) Agents", *J. Med. Chem.*, 30, pp. 1270-1278 (1987).

D. Huryn et al. "Synthesis of Iso-ddA, Member of a Novel Class of Anti-HIV Agents", *Tetrahedron Lett.*, 30, pp. 6259-6262 (1989).

D. Huryn et al. "Synthesis of Iso-ddA, Member of a Novel Class of Anti-HIV Agents: Dioxolane-T, A New 2',3'-Dideoxynucleoside Prototype with In Vitro Activity against HIV", *Chemtracts—Org. Chem.*, 3, pp. 249-251 (B. Ganem ed., 1990).

T. Lin et al., "Synthesis and Antiviral Activity of Various 3'-Azido, 3'-Amino, 2',3'-Unsaturated, and 2',3'-Dideoxy Analogues of Pyrimidine Deoxyribonucleosides against Retroviruses", *J. Med. Chem.*, 30, pp. 440-444 (1987).

H. Mitsuya et al., "3'-Azido-3'-deoxythymidine (BW 4509U): An Antiviral Agent that Inhibits the Infectivity and Cytopathic Effect of Human T-Lymphotropic Virus Type III/Lymphadenopathy-Associated Virus In Vitro", *Proc. Natl. Acad. Sci. USA*, 82, pp. 7096-7100 (1985).

H. Mitsuya & S. Broder, "Inhibition of the In Vitro Infectivity and Cytopathic Effect of Human T-Lymphotrophic Virus Type III/Lymphadenopathy-Associated Virus (HTLV-III/LAV) by 2',3'-Dideoxynucleosides", *Proc. Natl. Acad. Sci. USA*, 83, pp. 1911-1915 (1986).

D. Norbeck et al., (±)-Dioxolane-T ((±)-1-[(2β,4β)-2-(hydroxymethyl)-4-dioxolanyl]thymine), *Tetrahedron Lett.*, 30, pp. 6263-6266 (1989).

M. Wainberg et al., "Anti-HIV-1 Activity, Toxicity and Pharmacokinetics of Totally Novel Nucleoside Analogs", *V Intl. Conf. on AIDS Abs.*, M.C.P.63, p. 552 (1989).

M. Wainberg et al., "Characterization of AZT-Resistant Isolates of HIV-1: Susceptibility to Deoxythiacytidine and Other Nucleosides", *6th Intl. Conf. on AIDS Abs.*, 3, S.B.87, p. 117 (1990).

Belleau's Reply Brief at Final Hearing in Interference No. 104,201, Aug. 1999.

Belleau Brief for Final Hearing in Interference No. 104,201, Aug. 1999.

Liotta's Reply to Belleau Brief for Final Hearing (corrected copy submitted Sep. 29, 1999) in Interference No. 104,201.

Brief for Final Hearing of the Junior Party Liotta et al. in Interference No. 104,201, Sep. 1999.

Nov. 7, 1998 letter from B. Zacharie at BioChem to H. Nishimura at Daicel Chemical Industries, Ltd. along with a return letter from H. Nishimura. (Document ID: BCH 003382-85).

Apr. 13, 1989 letter from B. Zacharie to H. Nishimura and a Jun. 8, 1989 return letter from H. Nishimura. (Document ID: BCH 003389-92).

Apr. 20, 1989 letter from N.L. Cooper of Glaxo to J. McDonald of BioChem. (Document ID: G 10070-72).

Meeting report for the July 20-21, 1989 meeting between BioChem and Glaxo. (Document ID: G 10131-61).

Sep. 1989 BioChem report on its nucleoside research and development program. (Document ID: BCH 029913-19).

Circa Oct. 1989 handwritten preliminary report from B. Zacharie of BioChem. (Document ID: BCH 135971-74).

Nov. 14, 1989 letter from J. Wilson of Supelco, Inc. (U.S.) to J. Daley of Supelco Ltd. (Canada). (Document ID: BCH 001720-22).

Development proposal for BCH-189 submitted by Glaxo personnel on Dec. 8, 1989. (Document ID: G 10289-304).

BioChem summary of its research program in nucleoside analogs dated Dec. 15, 1989. (Document ID: G 10305-14).

Redacted copy of Dec. 15, 1989 summary of BioChem's research program in nucleoside analogs. (Document ID: BCH 029825-31).

Glaxo progress report dated Apr. 2, 1990 reflecting work conducted from Apr. 1989-Mar. 1990. (Document ID: G 10478-539).

Glaxo progress report dated Apr. 4, 1990 on the biological properties of the enantiomers of BCH-189. (Document ID: G 10558-73).

Copy of Apr. 4, 1990 Glaxo report regarding the biological properties of the enantiomers of BCH-189. (Document ID: BCH 031353-68).

Three letters: Jun. 1, 1990 letter from T. Mansour of BioChem to R. Storer of Glaxo; Apr. 26, 1989 letter from G.Dionne of BioChem to N.L. Cooper of Glaxo; Apr. 20, 1989 letter from N.L. Cooper at Glaxo to J. McDonald of BioChem. (Document ID: BCH 031305-11).

Aug. 10, 1990 Glaxo report titled "Separation of the Enantiomers of IAF BioChem Nucleosides." (Document ID: G 10965-75).

Copy of Aug. 10, 1990 Glaxo report regarding the separation of enantiomers of BCH-189. (Document ID: BCH 031342-52).

Oct. 9, 1990 Glaxo report on its enrichment of the enantiomers of BCH-189 using chiral acids accomplished during the Jun.-Jul. 1990 period. (Document ID: G 10948-50).

SUBSTITUTED-1,3-OXATHIOLANES AND SUBSTITUTED-1,3-DIOXOLANES WITH ANTIVIRAL PROPERTIES

This is a division of Ser. No. 08/306,380, filed Sep. 15, 1994, now abandoned, entitled SUBSTITUTED-1,3-OXATHIOLANES AND SUBSTITUTED-1,3-DIOXOLANES WITH ANTIVIRAL PROPERTIES which is a continuation of Ser. No. 07/564,160, filed Aug. 7, 1990, now abandoned, which is a continuation-in-part of Ser. No. 07/308,101, filed Feb. 8, 1989 (U.S. Pat. No. 5,047,407).

The present invention relates to novel substituted 1,3-oxathiolane and substituted-1,3-dioxolane cyclic compounds having pharmacological activity, to processes for and intermediates of use in their preparation, to pharmaceutical compositions containing them, and to the use of these compounds in the antiviral treatment of mammals.

Retroviral infections are a serious cause of disease, most notably, the acquired immunodeficiency syndrome (AIDS). The human immunodeficiency virus (HIV) has been recognized as the etiologic agent of AIDS, and compounds having an inhibitory effect against HIV multiplication have been actively sought.

Mitsuya et al., "3'-Azido-3'-deoxythymidine (BW A509U): An antiviral agent that inhibits the infectivity and cytopathic effect of human T-lymphotropic virus type III/lymphadenopathy-associated virus in vitro", Proc. Natl. Acad. Sci. U.S.A., 82, pp. 7096–7100 (1985), refers to a compound of formula (A) (3'-azido-2',3'-dideoxythymidine), commonly referred to as AZT. This compound is said to be useful in providing some protection for AIDS carriers against the cytopathogenic effect of immunodeficiency virus (HIV).

(A)

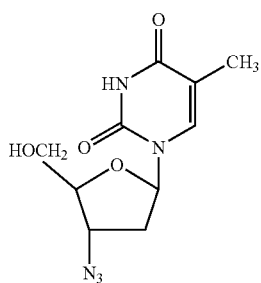

Mitsuya et al., "Inhibition of the in vitro infectivity and cytopathic effect of human T-lympho-trophic virus type III/lymphadenopathy-associated virus (HTLV-III/LAV) by 2'3'-dideoxynucleosides", Proc. Natl. Acad. Sci. U.S.A., 86, pp. 1911–15 (1986), have also referred to a group of 2',3'-dideoxynucleosides shown in formula (B) which are said to possess protective activity against HIV-induced cytopathogenicity.

(B)

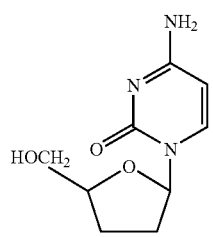

Balzarini et al., "Potent and selective anti-HTLV-III/LAV activity of 2',3'-dideoxycytidinene, the 2',3'-unsaturated derivative of 2',3'-dideoxycytidine", Biochem. Biophys. Res. Comm., 140, pp. 735–42 (1986), refer to an unsaturated analogue of these nucleosides—2',3'-dideoxycytidine, shown in formula (C)—as being characterized by antiretroviral activity.

(C)

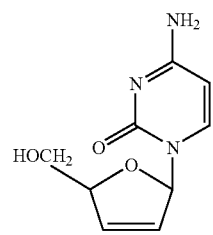

Baba et al., "Both 2',3'-dideoxythymidine and its 2',3'-unsaturated derivative (21,3'-dideoxy-thymidinene) are potent and selective inhibitors of human immunodeficiency virus replication in vitro", Biochem. Biophys. Res. Comm., 142, pp. 128–34 (1987), refer to the 2',3'-unsaturated analogue shown in formula (D) of 2',3'-dideoxythymidine. This analogue is purported to be a potent selective inhibitor of HIV replication.

(D)

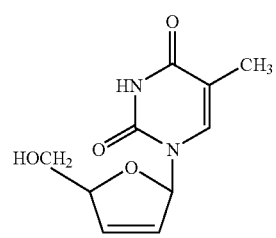

Analogues of AZT known as 3'-azido-2',3'-dideoxyuridine shown in formula (E), where Y is bromine or iodine, have been said to have an inhibitory activity against Moloney murine leukemia in T. S. Lin et al., "Synthesis and antiviral activity of various 3'-azido,3' amino,2',3'-unsaturated and 2',3'-dideoxy analogues of pyrimidine, deoxyribonucleosides against retroviruses", J. Med. Chem., 30, pp. 440–41 (1987).

(E)

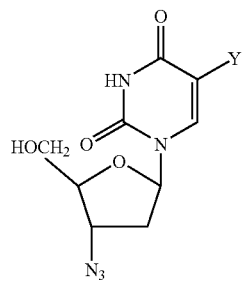

Finally, the 3'-fluoro analogues of 2',3'-dideoxycytidine shown in formula (F) and of 2',3'-dideoxythymidine shown in formula (G) are referred to in Herdewijn et al., "3'-Substituted 2',3'-dideoxynucleoside analogues as potential anti-HIV(HTLV-III/LAV) agents", J. Med. Chem., 30, pp. 1270–78 (1987), as having potent antiretroviral activity.

(F)

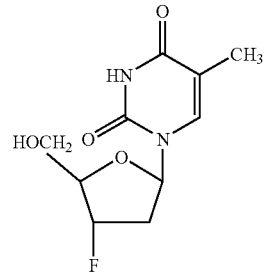

-continued

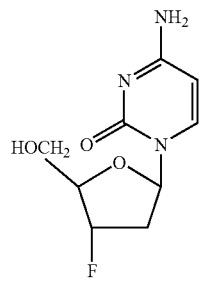
(G)

The most potent anti-HIV compounds thus far reported are 2',3'-dideoxynucleosides, more particularly, 2',3'-dideoxy cytidine (ddCyd) and 3'-azido-2',3'-dideoxythymidine (AzddThd or AZT). These compounds are also active against other kinds of retroviruses such as the Moloney murine leukemia virus. Because of the increasing incidence and the life-threatening characteristics of AIDS, efforts are being expended to discover and develop new non-toxic and potent inhibitors of HIV and blockers of its infectivity. It is therefore an object of the present invention to provide effective anti-HIV compounds of low toxicity and a synthesis of such new compounds that is readily feasible.

A structurally distinct class of compounds known as 2-substituted-5-substituted-1,3-oxathiolanes and 2-substituted-4-substituted-1,3-dioxolanes has now been discovered and found to have antiretroviral activity. In particular, these compounds have been found to act as non-toxic inhibitors of the replication of HIV-1 in T-lymphocytes over prolonged periods of time.

There are accordingly provided in a first aspect of this invention compounds of formula (I)

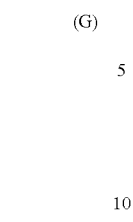
(I)

wherein $R_1$ is hydrogen or an acyl radical from 1 to 16 carbon atoms, preferably a benzoyl or a benzoyl substituted in any position by at least one halogen (bromine, chlorine, fluorine or iodine), $C_{1-6}$ alkyl, $C_{1-6}$ alkoxy, nitro or trifluoromethyl groups;

$R_2$ is a purine or pyrimidine base or an analogue or derivative thereof;

Z is O, S, S=O or $SO_2$; and pharmaceutically acceptable derivatives thereof.

It will be appreciated by those skilled in the art that the compounds of formula (I) contain at least two chiral centers (shown as * in formula (I)) and thus exist in the form of two pairs of optical isomers (i.e., enantiomers) and mixtures thereof including racemic mixtures. Thus the compounds of formula (I) may be either cis isomers, as represented by formula (II), or trans isomers, as represented by formula (III), or mixtures thereof. Each of the cis and trans isomers can exist as one of two enantiomers or as mixtures thereof including racemic mixtures. All such isomers and mixtures thereof including racemic mixtures are included within the scope of the invention.

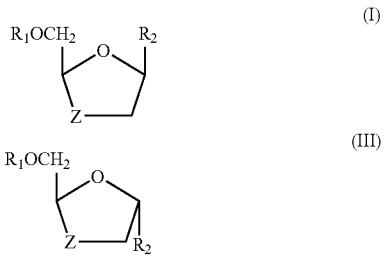

The compounds of formula (I) are preferably in the form of their cis isomers.

It will also be appreciated that when Z is S=O the compounds exist in two additional isomeric forms as shown in formulas (IIa) and (IIb) which differ in the configuration of the oxide oxygen atom relative to the 2,5-substituents. The compounds of the invention additionally embrace such isomers and mixtures thereof.

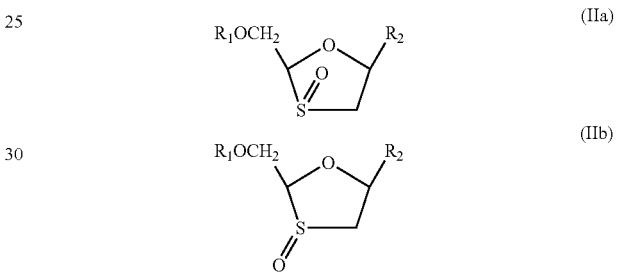

The purine or pyrimidine base or analogue or derivative thereof $R_2$ will be linked at the 9- or 1-position, respectively.

By "purine or pyrimidine base" or an analogue or derivative thereof is meant a purine or pyrimidine base found in native nucleosides or an analogue thereof which mimics such bases in that their structures (the kinds of atoms and their arrangement) are similar to the native bases but may either possess additional or lack certain of the functional properties of the native bases. Such analogues include those derived by replacement of a $CH_2$ moiety by a nitrogen atom (for example, 5-azapyrimidines such as 5-azacytosine) or vice verse (for example 7-deazapurines, for example 7-deazadenosine or 7-deazaguanosine) or both (e.g., 7-deaza-8-azapurines). By derivatives of such bases or analogues are meant those compounds wherein ring substituents are either incorporated, removed or modified by conventional substituents known in the art, e.g., halogen, hydroxyl, amino, $C_{1-6}$ alkyl. Such purine or pyrimidine bases, analogues and derivatives will be well known to those skilled in the art.

Conveniently the group $R_2$ is selected from:

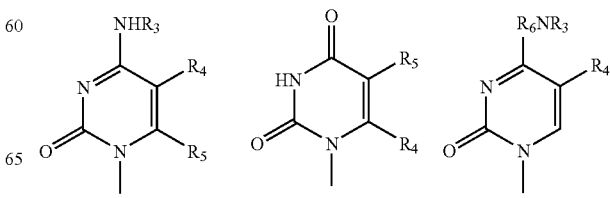

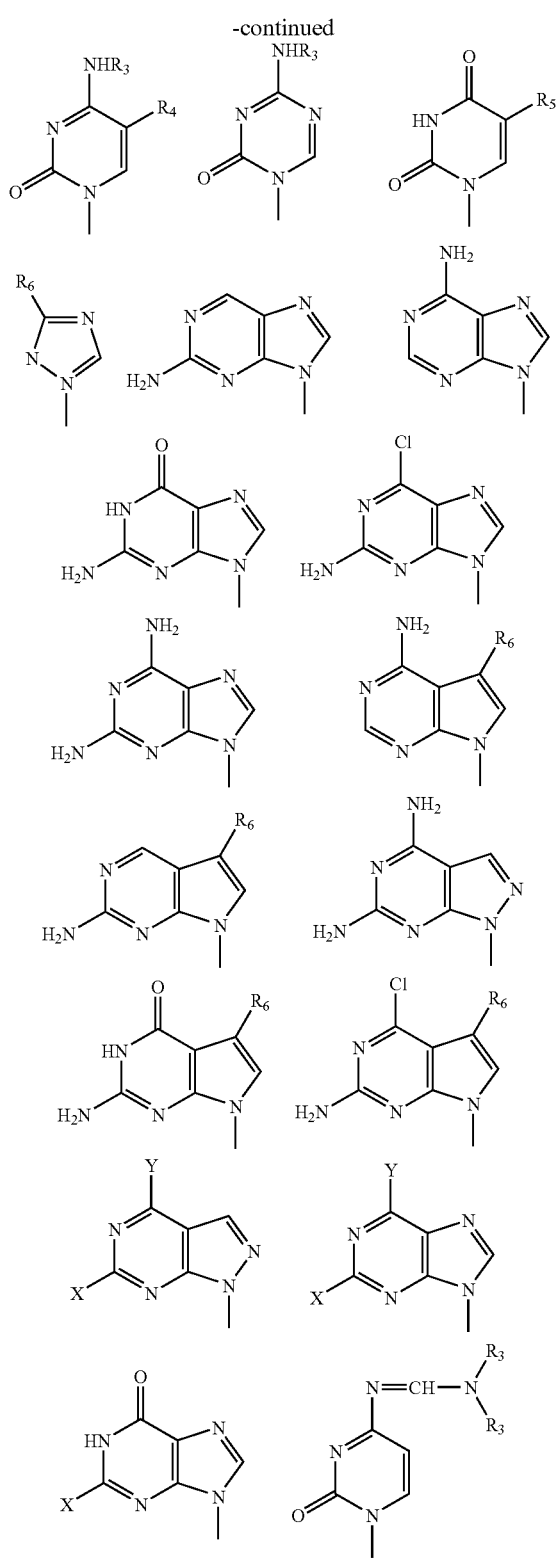

wherein $R_3$ is selected from the group of hydrogen, acetyl, hydroxyl or $C_{1-6}$ alkyl or alkenyl groups;

$R_4$ and $R_5$ are independently selected from the group of hydrogen, hydroxymethyl, trifluoromethyl, substituted or unsubstituted $C_{1-6}$ alkyl or alkenyl groups, bromine, chlo- rine, fluorine, or iodine; $R_6$ is selected from the group of hydrogen, cyano, carboxy, ethoxycarbonyl, carbamoyl, or thiocarbamoyl; and X and Y are independently selected from the group of hydrogen, bromine, chlorine, fluorine, iodine, amino or hydroxy groups.

Preferably $R_2$ is

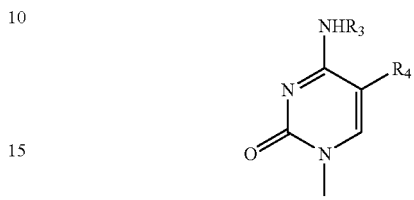

wherein $R_3$ and $R_4$ are as defined hereinabove.

Z is preferably —S—.

When the compound of formula (I) is a 1,3-oxathiolane of formula (Ia), where Z is S, S=O or $SO_2$,

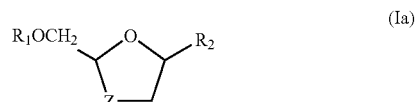

(Ia)

preferably:

$R_1$ is selected from a group consisting of hydrogen and an acyl group having 1 to 16 carbon atoms;

$R_2$ is a heterocyclic radical selected from the group consisting of:

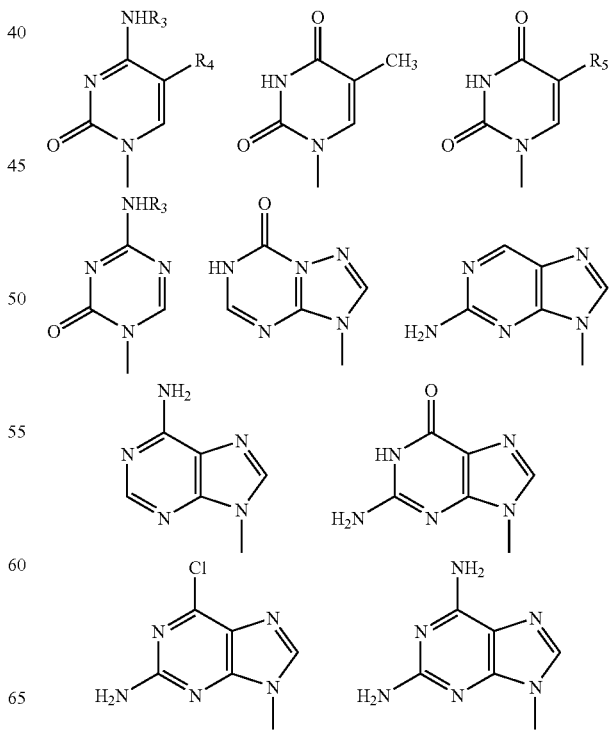

-continued

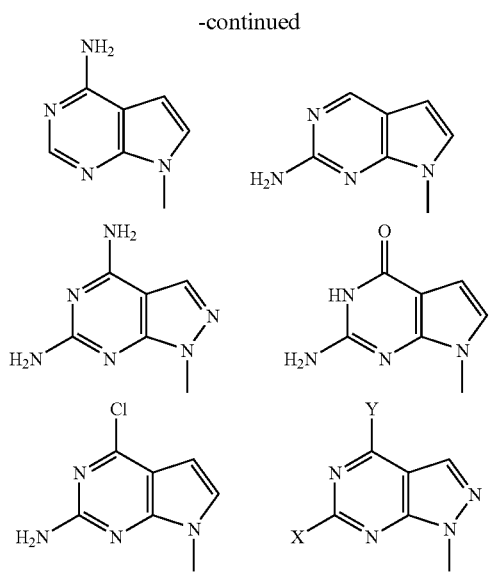

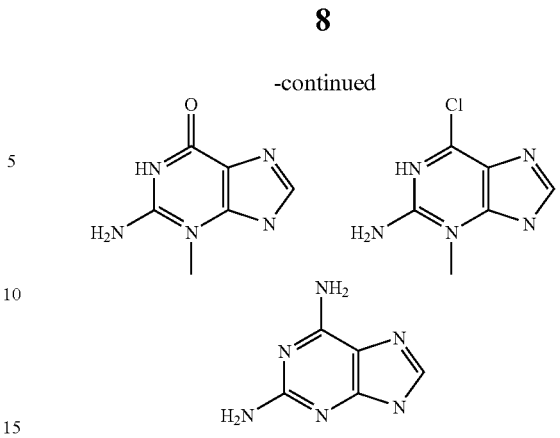

$R_3$ and $R_4$ are independently selected from the group consisting of hydrogen and $C_{1-6}$ alkyl groups;

$R_5$ is selected from the group consisting of hydrogen, $C_{1-6}$ alkyl, bromine, chlorine, fluorine, and iodine; and X and Y are independently selected from the group consisting of bromine, chlorine, fluorine, iodine, amino and hydroxyl groups.

When the compound of formula (I) is a 1,3-dioxolane of formula (Ib),

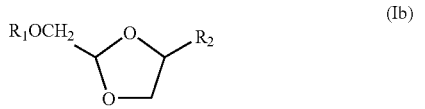

(Ib)

preferably:

$R_1$ is selected from the group consisting of hydrogen, an aliphatic acyl group having 1 to 16 carbon atoms, benzoyl and benzoyl substituted in any position by a halogen, a lower alkyl, a lower alkoxy, a nitro or a trifluoromethyl group;

$R_2$ is a heterocyclic radical selected from the group consisting of:

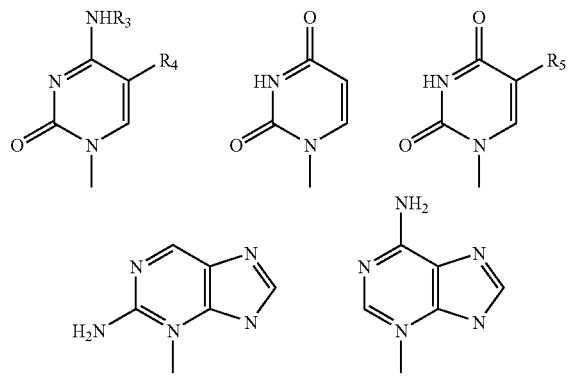

wherein:

$R_3$ is selected from the group consisting of hydrogen and lower alkyl radicals having from 1 to 3 carbon atoms;

$R_4$ is selected from the group consisting of hydrogen, lower alkyl and alkenyl radicals having from 1 to 3 carbon atoms; and $R_5$ is selected from the group consisting of lower alkyl and alkenyl radicals having from 1–3 carbon atoms, fluoro and iodo.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof, at functional groups in both the base moiety, $R_2$, and at the hydroxymethyl group of the oxathiolane or dioxolane ring. Modification at all such functional groups is included within the scope of the invention. However, of particular interest are pharmaceutically acceptable derivatives (e.g., esters) obtained by modification of the 2-hydroxymethyl group of the oxathiolane or dioxolane ring.

Preferred esters of the compounds of formula (I) include the compounds in which $R_1$ is replaced by a carboxyl function

in which the non-carbonyl moiety R of the ester grouping is selected from hydrogen, straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); substituted dihydro pyridinyl (e.g., N-methyldihyrdo pyridinyl); sulphonate esters such as alkyl- or aralkylsulphonyl (e.g., methanesulphonyl); sulfate esters; amino acid esters (e.g., L-valyl or L-isoleucyl) and mono-, di- or tri-phosphate esters.

Also included within the scope of such esters are esters derived from polyfunctional acids such as carboxylic acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters are well known. See, for example, Hahn et al., "Nucleotide Dimers as Anti-Human Immunodeficiency Virus Agents", *Nucleotide Analogues*, pp. 156–159 (1989) and Busso et al., "Nucleotide Dimers Suppress HIV Expression In Vitro", *AIDS Research and Human Retroviruses*, 4(6), pp. 449–455 (1988). Where esters are derived from such acids, each acidic group is preferably esterified by a compound of formula (I) or other nucleosides or analogues and derivatives thereof to provide esters of the formula (IV) where:

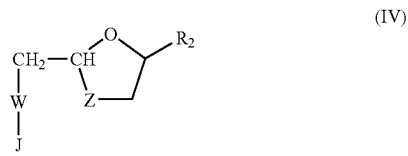

(IV)

W is

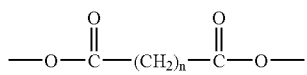

and n is an integer of 1 to 10 or

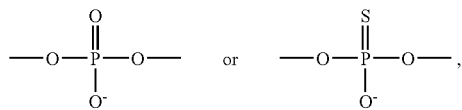

J is any nucleoside or nucleoside analog or derivative thereof and Z and $R_2$ are as defined above. Among the preferred nucleosides and nucleoside analogues are 3'-azido-2'3'-dideoxy-thymidine, 2',3'-dideoxycytidine, 2',3'-dideoxyadenosine, 2',3'-dideoxyinosine, 2',3'-dideoxythymidine, 2',3'-dideoxy-2',3'-didehydrothymidine, and 2',3'-dideoxy-2',3'-didehydrocytidine and ribavirin and those nucleosides whose bases are depicted on pages 7–8 of this specification. We most prefer a homodimer consisting of two nucleosides of formula (I).

With regard to the above described esters, unless otherwise specified, any alkyl moiety present advantageously contains 1 to 16 carbon atoms, preferably 1 to 4 carbon atoms and could contain one or more double bonds. Any aryl moiety present in such esters advantageously comprises a phenyl group.

In particular the esters may be a $C_{1-16}$ alkyl ester, an unsubstituted benzoyl ester or a benzoyl ester substituted by at least one halogen (bromine, chlorine, fluorine or iodine), $C_{1-6}$ alkyl or alkenyl, saturated or unsaturated $C_{1-6}$ alkoxy, nitro or trifluoromethyl groups.

Pharmaceutically acceptable salts of the compounds of formula (I) include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $NR_4+$ (where R is $C_{1-4}$ alkyl) salts.

References hereinafter to a compound according to the invention include both compounds of formula (I) and their pharmaceutically acceptable derivatives.

Specific compounds of formula (I) include:
Cis-2-hydroxymethyl-5-(cytosin-1'-yl)-1,3-oxathiolane, trans-2-hydroxymethyl-5-(cytosin-1'-yl)-1,3-oxathiolane, and mixtures thereof;
Cis-2-benzoyloxymethyl-5-(cytosin-1'-yl)-1,3-oxathiolane, trans-2-benzoyloxymethyl-5-(cytosin-1'-yl)-1,3-oxathiolane, and mixtures thereof;
Cis-2-hydroxymethyl-5-($N_4$'-acetyl-cytosin-1'-yl)-1,3-oxathiolane, trans-2-hydroxymethyl-5-($N_4$'-acetyl-cytosin-1'-yl)-1,3-oxathiolane, and mixtures thereof;
Cis-2-benzoyloxymethyl-5-($N_4$'-acetyl-cytosin-1'-yl)-1,3-oxathiolane, trans-2-benzoyloxymethyl-5-($N_4$'-acetyl-cytosin-1'-yl)-1,3-oxathiolane, and mixtures thereof; and
Cis-2-hydroxymethyl-5-(cytosin-1'-yl)-3-oxo-1,3-oxathiolane;
Cis-2-hydroxymethyl-5-(N-dimethylamino-methylene cytosin-1'-yl)-1,3-oxathiolane;
Bis-Cis-2-succinyloxymethyl-5-(cytosin-1'-yl)-1,3-oxathiolane;
Cis-2-benzoyloxymethyl-5-(6'-chloropurin-N-9'-yl)-1,3-oxathiolane; trans-2-benzoyloxymethyl-5-(6'-chloropurin-N-9'-yl)-1,3-oxathiolane, and mixtures thereof;
Cis-2-hydroxymethyl-5-(6'-hydroxypurin-N-9'-yl)-1,3-oxathiolane; trans-2-hydroxymethyl-5-(6'-hydroxypurin-N-9'-yl)-1,3-oxathiolane; and mixtures thereof.
Cis-2-benzoyloxymethyl-5-(uracil-N-1'-yl)-1,3-oxathiolane, trans-2-benzoyloxymethyl-5-(uracil-N-1'-yl)-1,3-oxathiolane, and mixtures thereof;
Cis-2-hydroxymethyl-5-(uracil-N-1'-yl)-1,3-oxathiolane;
Cis-2-benzoyloxymethyl-5-(thymin-N-1'-yl)-1,3-oxathiolane, trans-2-benzoyloxymethyl-5-(thymin-N-1'-yl)-1,3-oxathiolane, and mixtures thereof;
Cis-2-hydroxymethyl-5-(thymin-N-1'-yl)-1,3-oxathiolane;
Cis-2-hydroxymethyl-5-(adenin-9'-yl)-1,3-oxathiolane, trans-2-hydroxymethyl-5-(adenin-9'-yl)-1,3-oxathiolane, and mixtures thereof;
Cis-2-hydroxymethyl-5-(inosin-9'-yl)-1,3-oxathiolane, trans-2-hydroxymethyl-5-(inosin-9'-yl)-1,3-oxathiolane, and mixtures thereof;
Cis-2-benzoyloxymethyl-5-($N_4$'-acetyl-5'-fluorocytosin-1'-yl)-1,3-oxathiolane, trans-2-benzoyloxymethyl-5-($N_4$'-acetyl-5'-fluorocytosin-1'-yl)-1,3-oxathiolane, and mixtures thereof;
Cis-2-hydroxymethyl-5-(5'-fluorocytosin-1'-yl)-1,3-oxathiolane, trans-2-hydroxymethyl-5-(5'-fluorocytosin-1'-yl)-1,3-oxathiolane, and mixtures thereof;
Cis-2-acetoxymethyl-4-(thymin-1'-yl)-1,3-dioxolane, trans-2-acetoxymethyl-4-(thymin-1'-yl)-1,3-dioxolane, and mixtures thereof;
Cis-2-hydroxymethyl-4-(thymin-1'-yl)-1,3-dioxolane, trans-2-hydroxymethyl-4-(thymin-1'-yl)-1,3-dioxolane, and mixtures thereof;
Cis-2-benzoyloxymethyl-4-(cytosin-1'-yl)-1,3 dioxolane, trans-2-benzoyloxymethyl-4-(cytosin-1'-yl)-1,3 dioxolane, and mixtures thereof;

Cis-2-hydroxymethyl-4-(cytosin-1'-yl)-1,3-dioxolane, trans-2-hydromethyl-4-(cytosin-1'-yl)-1,3-dioxolane, and mixtures thereof;

Cis-2-benzoyloxymethyl-4-(adenin-9'-yl)-1,3-dioxolane, trans-2-benzoyloxymethyl-4-(adenin-9'-yl)-1,3-dioxolane, and mixtures thereof;

Cis-2-hydroxymethyl-4-(adenin-9'-yl)-1,3-dioxolane, trans-2-hydroxymethyl-4-(adenin-9'-yl)-1,3-dioxolane, and mixtures thereof;

Cis-2-benzoyloxylmethyl-4-(2'-amino-6'-chloro-purin-9'-yl)-1,3-dioxolane, trans-2-benzoyloxylmethyl-4-(2'-amino-6'-chloro-purin-9'-yl)-1,3-dioxolane, and mixtures thereof;

Cis-2-hydroxymethyl-4-(2'-amino-6'-chloro-purin-9'-yl)-1,3-dioxolane, trans-2-hydroxymethyl-4-(2'-amino-6'-chloro-purin-9'-yl)-1,3-dioxolane, and mixtures thereof;

Cis-2-hydroxymethyl-4-(2'-amino-purin-9'-yl)-1,3-dioxolane, trans-2-hydroxymethyl-4-(2'-amino-purin-9'-yl)-1,3-dioxolane, and mixtures thereof;

Cis-2-hydroxymethyl-4-(2',6'-diamino-purin-9'-yl)-1,3-dioxolane, trans-2-hydroxymethyl-4-(2',6'-diamino-purin-9'-yl)-1,3-dioxolane, and mixtures thereof;

Cis-2-hydroxymethyl-4-(guanin-9'-yl)-1,3-dioxolane, trans-2-hydroxymethyl-4-(guanin-9'-yl)-1,3-dioxolane, and mixtures thereof;

Cis-2-hydroxymethyl-5-(N-dimethylamino methylene cytosin-1'-yl)-1,3-dioxolane, trans-2-hydroxymethyl-4-(N-dimethylamino methylene cytosin-1'-yl)-1,3-dioxolane, and mixtures thereof;

in the form of a racemic mixture or a single enantiomer.

The compounds of the invention either themselves possess antiviral activity and/or are metabolizable to such compounds. In particular these compounds are effective in inhibiting the replication of retroviruses, including human retroviruses such as human immunodeficiency viruses (HIV's), the causative agents of AIDS.

There is thus provided as a further aspect of the invention a compound formula (I) or a pharmaceutically acceptable derivative thereof for use as an active therapeutic agent in particular as an antiviral agent, for example in the treatment of retroviral infections.

In a further or alternative aspect there is provided a method for the treatment of a viral infection, in particular an infection caused by a retrovirus such as HIV, in a mammal, including man, comprising administration of an effective amount of an antiviral compound of formula (I) or a pharmaceutically acceptable derivative thereof.

There is also provided in a further or alternative aspect of this invention, use of a compound of formula (I) or a pharmaceutically acceptable derivative thereof for the manufacture of a medicament for the treatment of a viral infection.

The compounds of the invention are also useful in the treatment of AIDS-related conditions such as AIDS-related complex (ARC), persistent generalized lymphadenopathy (PGL), AIDS-related neurological conditions (such as dementia), anti-HIV antibody-positive and HIV-positive conditions, Kaposi's sarcoma, thrombocytopenia purpurea and opportunistic infections.

The compounds of the invention are also useful in the prevention or progression to clinical illness of individuals who are anti-HIV antibody or HIV-antigen positive and in prophylaxis following exposure to HIV.

The compounds of formula (I) or the pharmaceutically acceptable derivatives thereof, may also be used for the prevention of viral contamination of biological fluids such as blood or semen in vitro.

Certain of the compounds of formula (I) are also useful as intermediates in the preparation of other compounds of the invention.

It will be appreciated by those skilled in the art that references herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general, however, a suitable dose will be in the range from about 1 to about 750 mg/kg of body weight per day, such as 3 to about 120 mg per kilogram body weight of the recipient per day, preferably in the range of 6 to 90 mg/kg/day, most preferably in the range of 15 to 60 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to 75 µM, preferably about 2 to 50 µM, most preferably about 3 to about 30 µM. This may be achieved, for example, by the intravenous injection of a 0.1 to 5% solution of the active ingredient, optionally in saline, or administered as a bolus containing about 0.1 to about 110 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers thereof and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

The compounds according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored based, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutically formulations suitable for rectal administration wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

The compounds of the invention may also be used in combination with other therapeutic agents, for example, other antiinfective agents. In particular the compounds of the invention may be employed together with known antiviral agents.

The invention thus provides, in a further aspect, a combination comprising a compound of formula (I) or a physiologically acceptable derivative thereof together with another therapeutically active agent, in particular, an antiviral agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

Suitable therapeutic agents for use in such combinations include acyclic nucleosides such as acyclovir, ganciclovir, interferons such as alpha-, beta-and gamma-interferon; glucuronation inhibitors such as probenecid; nucleoside transport inhibitors such as dipyridamole; nucleoside analogues such as 3'-azido-2',3'-dideoxythymidine, 2',3'-dideoxycytidine, 2',3'-dideoxyadenosine, 2',3'-dideoxyinosine, 2',3'-dideoxythymidine, 2',3'-dideoxy-2',3'-didehydro-thymidine, and 2',3'-dideoxy-2',3'-didehydrocytidine and ribavirin; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments and CD4-hybrid molecules.

The individual components of such combinations may be administered either sequentially or simultaneously in separate or combined pharmaceutical formulations.

When the compound of formula (I) or a pharmaceutically acceptable derivative thereof is used in combination with a second therapeutic agent active against the same virus, the dose of each compound may be either the same or differ from that when the compound is used alone. Appropriate doses will be readily appreciated by those skilled in the art.

In the processes for preparing the compounds of this invention, the following definitions are used:

$R_1$ is a hydrogen, an acyl group having from 1 to 16 carbon atoms, or a hydroxyl protecting group;

$R_2$ is a purine or pyrimidine base or an analogue or derivative thereof;

$R_x$ is substituted or unsubstituted $C_{1-6}$ alkyl;

$R_y$ is substituted or unsubstituted $C_{1-6}$ alkyl or substituted or unsubstituted aryl;

$R_z$ is halo, such as bromo, chloro, iodo or fluoro; and

R is a substituted or unsubstituted, saturated or unsaturated alkyl group, e.g., a $C_{1-6}$ alkyl or alkenyl group (such as methyl, ethyl, propyl, butyl, ethenyl, propenyl, allyl, butenyl, etc.); a substituted or unsubstituted aliphatic or aromatic acyl group, e.g., a $C_{1-6}$ aliphatic acyl group such as acetyl or an aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidate group such as trichloroacetamidate; substituted or unsubstituted, saturated or unsaturated phosphonate, such as diethylphosphonate; substituted or unsubstituted aliphatic or aromatic sulphonyl group, such as tosylate; or hydrogen.

Oxathiolane compounds of formula (Ia), i.e., compounds of formula (I) wherein Z is S, S=O or $SO_2$, and their pharmaceutically acceptable derivatives may be prepared according to the processes discussed herein or by any method known in the art for the preparation of compounds of analogous structure.

One process according to the invention is illustrated in SCHEME 1. Although this process is illustrated using specific reagents and compounds, it will be obvious to one of skill in the art that suitable alternative reactants may be used to prepare analogous products as depicted, for example, in SCHEME 1A.

The various steps involved in the synthesis as illustrated in SCHEME 1 may be briefly described as follows:

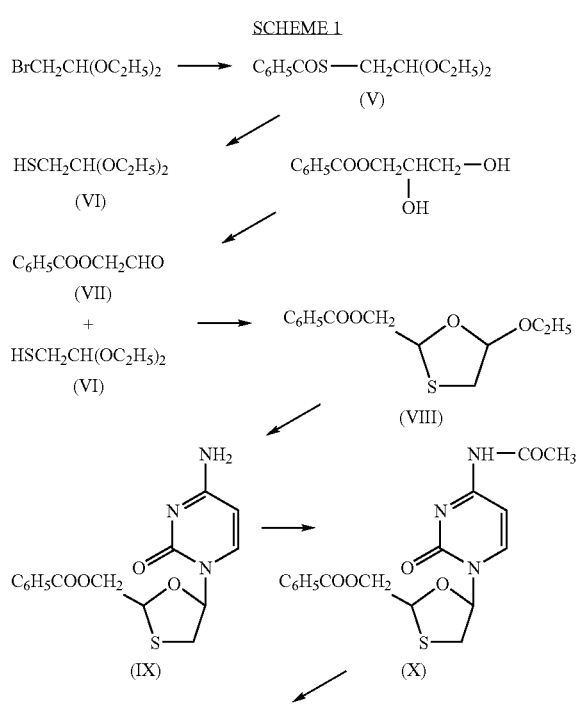

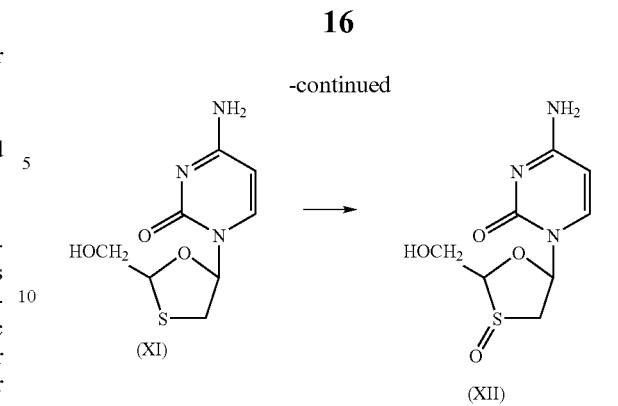

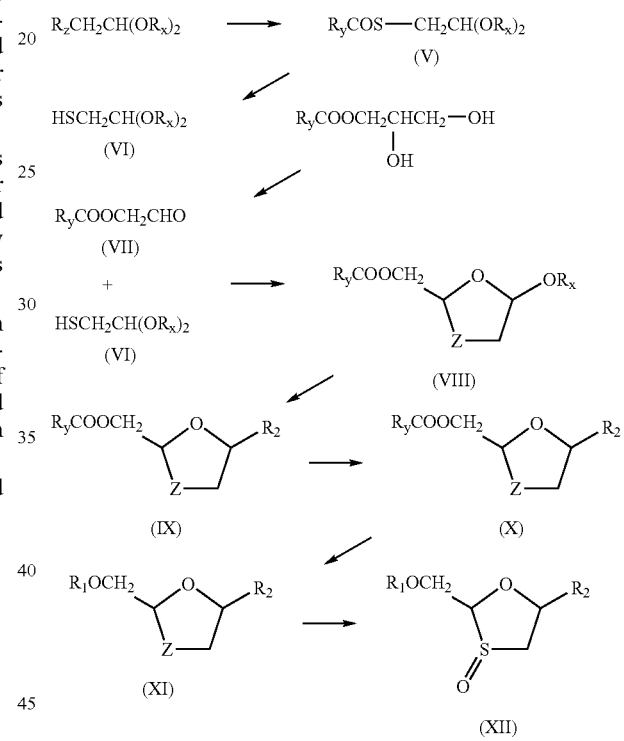

Step 1: Commercial bromoacetaldehyde diethyl acetal (or an analogous halo alkyl acetal of the formula $R_zCH_2(OR_x)_2$), is treated in boiling DMF with an excess of potassium thiobenzoate to give the benzoylthio acetal of formula (V).

Step 2: The benzoyl group of formula (V) is hydrolyzed with sodium hydroxide in an aqueous organic solvent to give the known mercaptoacetal shown in formula (VI) (G. Hesse and I. Jorder, "Mercapto-acetaldehyde and dioxy-1,4-dithiane", Chem. Ber., 85, pp. 924–32 (1952)).

Step 3: Glycerol 1-monobenzoate prepared according to the literature (E. G. Hallonquist and H. Hibbert, "Studies on reactions relating to carbo-hydrates and polysaccharides. Part XLIV: Synthesis of isomeric bicyclic acetal ethers", Can. J. Research, 8, pp. 129–36 (1933)), is oxidized with sodium meta-periodate to give the known benzoyloxyacetaldehyde of formula (VII) (C. D. Hurd and E. M. Filiachione, "A new approach to the synthesis of aldehyde sugars", J. Am. Chem. Soc., 61, pp. 1156–59 (1939)).

Step 4: The aldehyde of formula (VII) or any aldehyde of the formula $R_yCOOCH_2CHO$ is then condensed with the mercaptoacetal of formula (VI) or any mercaptoacetal of the formula $HSCH_2CH(OR_x)_2$ in a compatible organic solvent, such as toluene, containing a catalytic amount of a strong acid to give the novel intermediate shown in formula (VIII).

Step 5: The 1,3-oxathiolane of formula (VIII) is then reacted with a purine or pyrimidine base (e.g., cytosine) previously silylated with, for example, hexamethyldisilazane in a compatible solvent using a Lewis acid or trimethylsilyl triflate to give intermediate of formula (IX).

Step 6: The amine function of the compound shown in formula (IX) is acetylated with acetic anhydride to yield the intermediate of formula (X) as cis- and trans-isomers which are separated, preferably by fractional crystallization, to give pure cis-(X) and pure trans-(X).

Step 7: The cis- or trans-isomers of formula (X) are treated with methanolic ammonia to obtain the desired product shown in formula (XI) as cis- and trans-isomers.

Step 8: The preceding isomers of formula (XI) are treated with an oxidizing agent which may be a suitable peracid in a compatible solvent to give the 5-oxide (sulfoxide) of formula (XII).

This synthesis is applicable to any nucleoside base analogue, as would be obvious to those skilled in the art of nucleoside chemistry. Other compounds defined by formula (Ia) may be obtained similarly from intermediate VII by using the appropriate heterocyclic compound in place of cytosine in Step 5. In Step 4, other esters of hydroxyacetaldehyde such as aliphatic acyl or substituted aroyl groups can be used following the same sequence of steps leading to the compounds of formula (XI) and formula (XII), respectively.

A second process according to this invention for producing oxathiolane compounds is illustrated in SCHEME 2. Although this process is illustrated using specific reagents and compounds, it will be obvious to one of skill in the art that suitable analogous reactants may be used to prepare analogous products, as depicted, for example, in SCHEME 2A.

The various steps involved in the synthesis as illustrated in SCHEME 2 may be briefly described as follows:

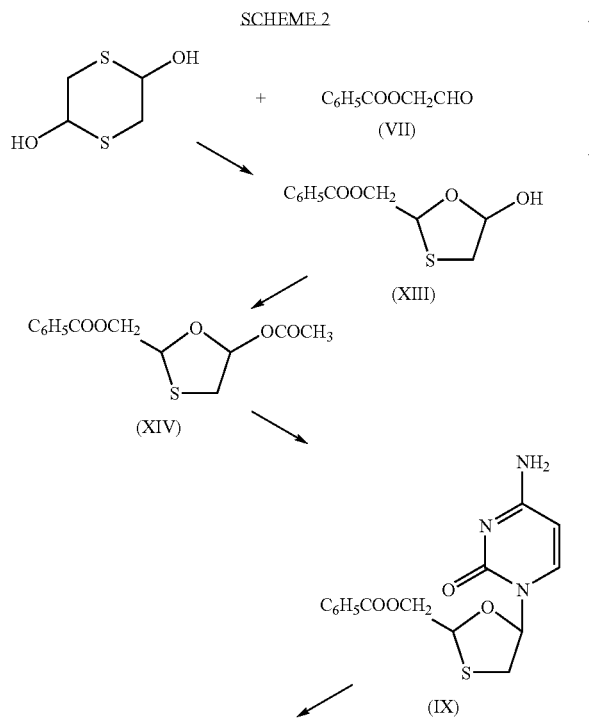

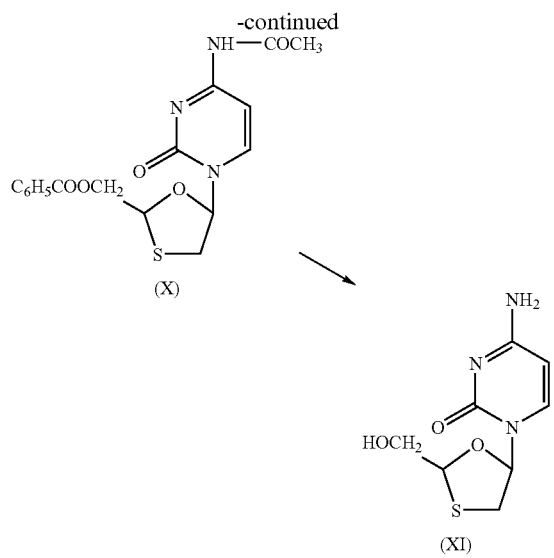

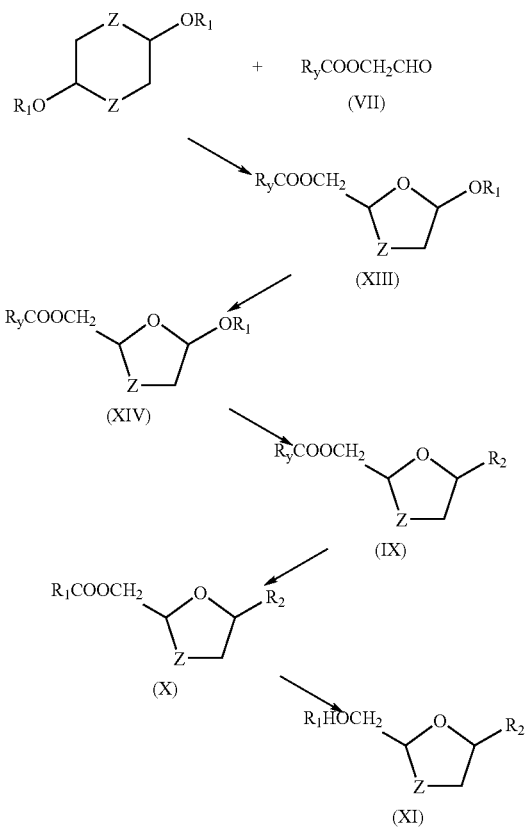

Step 1: A mercaptoacetaldehyde monomer produced from the dimer in a solvent such as pyridine is reacted directly with a benzoyloxyacetaldehyde of formula (VII) or any aldehyde of the formula $R_yCOOCH_2CHO$ to yield an oxathiolane lactol of formula (XIII).

Step 2: The hydroxyl group of the compound of formula (XIII) is converted to a leaving group with a suitable reagent such as acetyl chloride in a compatible organic solvent to yield an important oxathiolane intermediate of formula (XIV).

Step 3: The oxathiolane intermediate of formula (XIV) is reacted with a previously silylated purine or pyrimidine base to give, for example, a cytosin-1'-yl oxathiolane of formula (IX).

Step 4: The amine function of the compound shown in formula (IX) is acylated with acetic anhydride in a solvent such as pyridine to yield a compound of formula (X) which provides for easier separation of isomers.

Step 5: The benzoate and acetyl functions of the compound of formula (X) are hydrolyzed under basic conditions to yield an oxathiolane of formula (XI).

A third process for producing oxathiolane compounds is illustrated in SCHEME 3. Although this process is illustrated using specific reagents and compounds, it will be obvious to one of skill in the art that suitable analogous reactants may be used to prepare analogous products, as depicted, for example, in SCHEME 3A.

The various steps involved in the synthesis as illustrated in SCHEME 3 may be briefly described as follows:

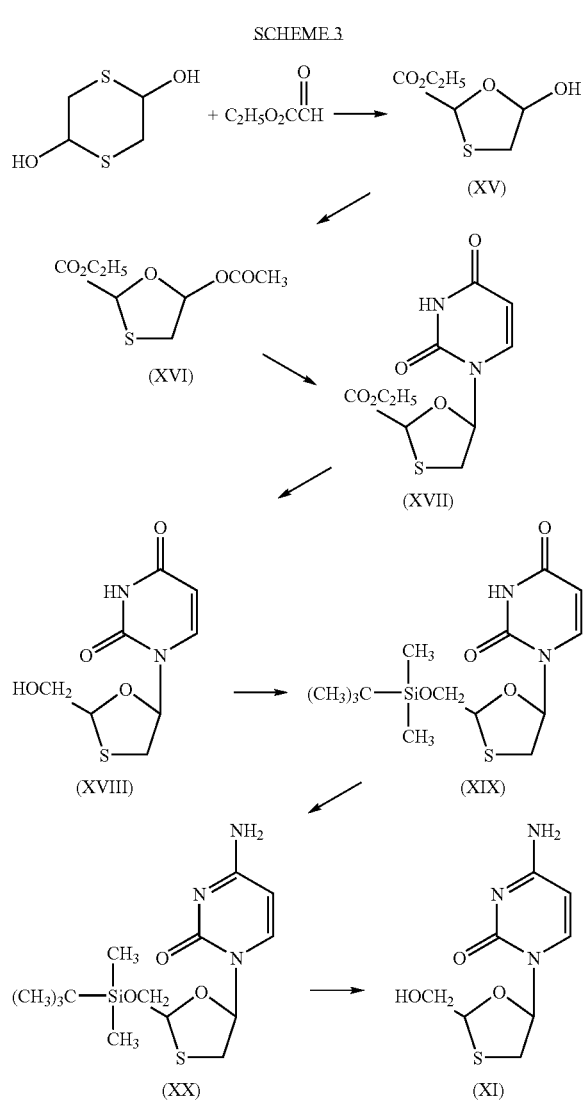

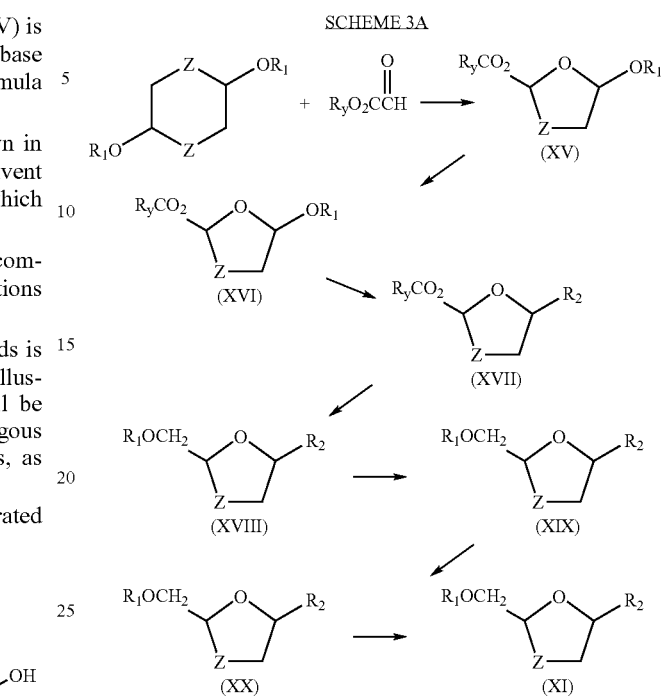

Step 1: Mercaptoacetaldehyde monomer produced from the dimer in a solvent such as pyridine is reacted directly with ethyl glyoxylate or any organic glyoxylate of the formula $R_yOOCCHO$ to yield an oxathiolane lactol of formula (XV).

Step 2: The hydroxyl group of the compound of formula (XV) is converted to a leaving group with a suitable reagent such as acetyl chloride in a compatible organic solvent to yield an important oxathiolane intermediate of formula (XVI).

Step 3: The oxathiolane intermediate of formula (XVI) is reacted with a previously silylated purine or pyrimidine base, e.g., uracil, in the presence of a Lewis acid or preferably trimethylsilyl iodide to give, e.g., a uracil-1'-yl oxathiolane of formula (XVII) predominantly as the cis-isomer.

Step 4: The ester group of the oxathiolane of formula (XVII) is selectively reduced with a suitable reducing agent such as sodium borohydride in a compatible organic solvent such as methanol to yield an oxathiolane nucleoside of formula (XVIII).

Step 5: The hydroxyl group of the compound of formula (XVIII) is protected with a suitable silyl protecting group such as t-butyl-dimethyl silyl in an appropriate solvent such as dimethyl formamide (DMF) to yield an oxathiolane of formula (XIX).

Step 6: The uracil base of formula (XIX) can be interconverted to another base, such as cytosine, by reaction with a suitable reagent such as p-chlorophenoxy phosphorous oxychloride followed by amination with, e.g., ammonia in methanol to yield an oxathiolane of formula (XX).

Step 7: The silyl group of the compound of formula (XX) is removed under neutral conditions using a suitable reagent such as tetra n-butyl ammonium fluoride in a suitable solvent such as tetrahydrofuran to yield the oxathiolane of formula (XI).

A fourth process according to this invention for producing oxathiolane compounds is illustrated in SCHEME 4. Although this process is illustrated using specific reagents and compounds, it will be obvious to one of skill in the art that suitable analogous reactants may be used to prepare analogous products, as depicted, for example, in SCHEME 4A.

The various steps involved in the synthesis as illustrated in SCHEME 4 may be briefly described as follows:

SCHEME 4

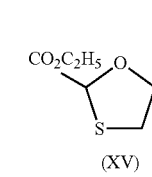
(XV)

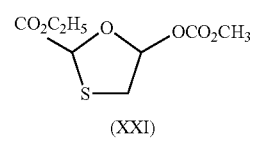
(XXI)

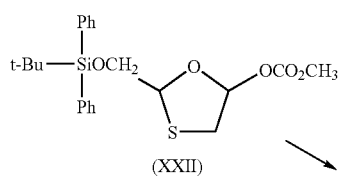
(XXII)

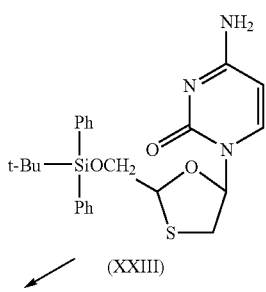
(XXIII)

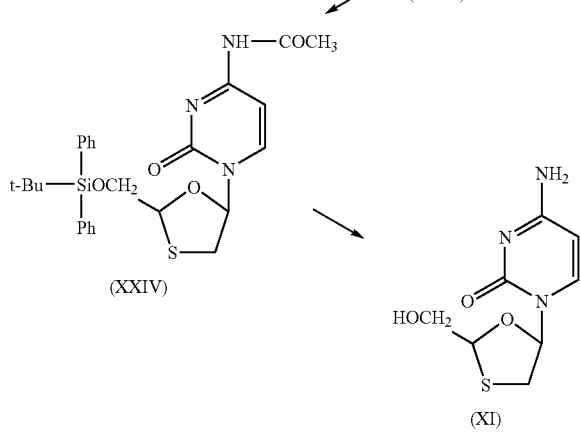
(XXIV)

(XI)

SCHEME 4A

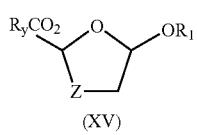
(XV)

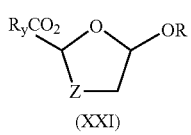
(XXI)

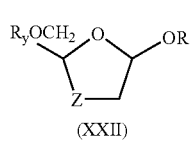
(XXII)

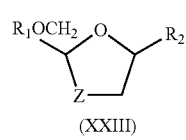
(XXIII)

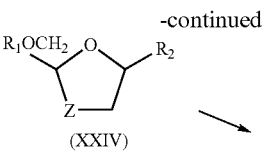
(XXIV)

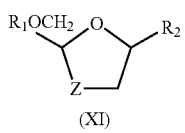
(XI)

Step 1: The hydroxyl group of the intermediate of formula XV, or corresponding $R_y$-substituted intermediate (see SCHEME 3, step 1), is converted to a leaving group with a suitable reagent such as methyl chloroformate in a compatible organic solvent to yield an important intermediate of formula (XXI).

Step 2: The ester group of the intermediate of formula (XXI) is selectively reduced with a suitable reducing agent such as sodium borohydride in a compatible organic solvent such as methanol and the resultant hydroxyl group is directly protected with a suitable group such as t-butyl diphenyl silyl to yield an oxathiolane of formula (XXII).

Step 3: The oxathiolane of formula (XXII) is reacted with a previously silylated purine or pyrimidine base, such as cytosine to give, e.g., a cytosin-1'-yl oxathiolane of formula (XXIII).

Step 4: The amine function of the compound shown in formula (XXIII) is acylated, e.g., with acetic anhydride in a solvent such as pyridine to yield a compound of formula (XXIV) which provides for easier separation of isomers.

Step 5: The silyl and acetyl functions of the compound of formula (XXIV) are hydrolyzed under basic conditions to yield an oxathiolane of formula (XI).

In a fifth process the oxathiolane compounds of formula (Ia), in which Z is S, S=O or $SO_2$, may be prepared by the reaction of a compound of formula (LIX)

(LIX)

with a compound of formula (LX)

(LX)

wherein P is a protecting group, followed by removal of the protecting group. The compounds of formula (LIX) may be prepared for reaction by a suitable epoxide (LXI)

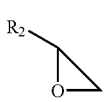
(LXI)

with an appropriate sulphur-containing compound, e.g., sodium thioacetate. Compounds of formula (LXI) are either known in the art or may be obtained by analogous processes.

In a sixth process of this invention, the oxathiolane compounds of formula (Ia) may be made by converting an intermediate of formula (LXII)

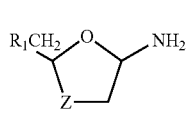
(LXIII)

to a compound of formula (Ia) by conversion of the anomeric $NH_2$ to the desired purine or pyrimidine base by methods well known in the art of nucleoside chemistry.

The dioxolane compounds of formula (Ib) and their pharmaceutically acceptable derivatives may be prepared by the processes according to this invention or by any method known in the art for preparation of compounds of analogous structure.

One such process for preparing dioxolane compounds of formula (Ib) is outlined in SCHEME 5. Although this process is illustrated using specific reagents and compounds, it will be obvious to one of skill in the art that suitable alternative reactants may be used to prepare analogous products, as depicted, for example, in SCHEME 5A.

The various steps involved in the synthesis illustrated in SCHEME 5 may be briefly described as follows:

SCHEME 5

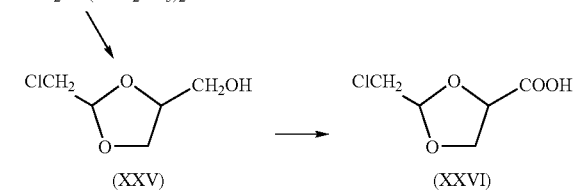
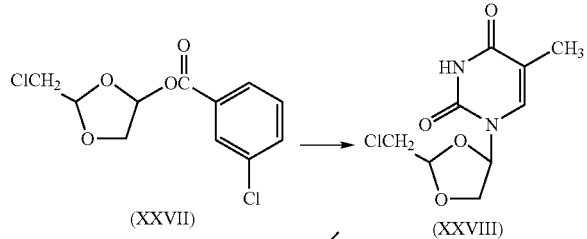
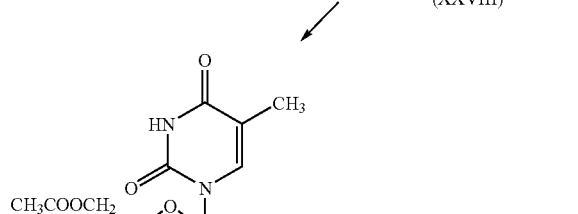
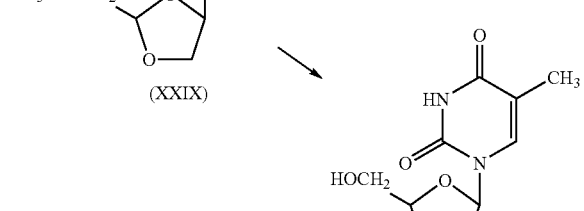

SCHEME 5A

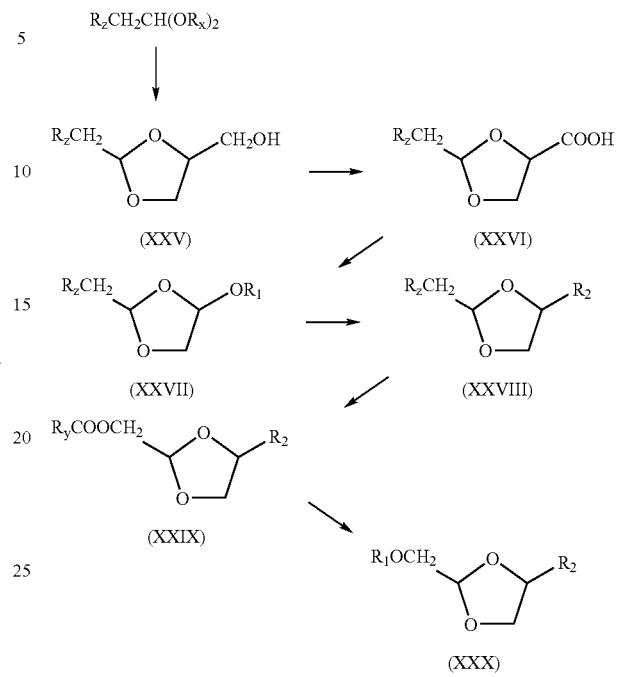

Step 1: Chloroacetaldehyde diethyl acetal (or an analogous halo alkyl acetal) is treated with glycerol in an inert solvent according to the procedure reported by E. G. Hallonquist and H. Hibbert, "Studies In Reactions Relating To Carbohydrates And Polysaccharides—Part XLIV: Synthesis Of Isomeric Bicyclic Acetal Ethers", Can. J. Res., 8, pp. 129–136 (1933) to produce an intermediate of formula (XXV).

Step 2: The primary alcohol function of the dioxolane intermediate of formula (XXV) is treated with an oxidizing reagent such as chromic acid (which may be complexed with pyridine) in a compatible organic solvent to give the corresponding dioxolane carboxylic acid of formula (XXVI).

Step 3: The acid of formula (XXVI) is converted to a mixed anhydride using an alkyl chloroformate and subjected to a Bayer-Villiger oxidation with an organic peracid such as m-chloroperbenzoic acid to yield the corresponding aroyloxydioxolane of formula (XXVII).

Step 4: Intermediate of formula (XXVII) is then reacted with previously silylated purine or pyrimidine base such as thymine, with, e.g., hexamethyldisilazane in a compatible solvent and the reaction catalyzed by a Lewis acid or preferably by trimethylsilyl triflate to give, e.g., the thymin-1'-yl dioxolane of formula (XVI).

Step 5: The chlorine atom of formula (XXVIII) is displaced by reaction with a benzoic acid salt in a compatible solvent such as dimethyl formamide to give an intermediate of formula (XXIX).

Step 6: The benzoate ester function is then hydrolyzed under basic conditions to yield the desired end-product of formula (XXX).

A second process for preparing further specific dioxolane compounds of the present invention is illustrated in SCHEME 6. Although this process is illustrated using specific reagents and compounds, it will be obvious to one of skill in the art that suitable alternative reactants may be used to prepare analogous products, as depicted, for example, in SCHEME 6A.
The various steps involved in the synthesis illustrated in SCHEME 6 may be briefly described as follows:
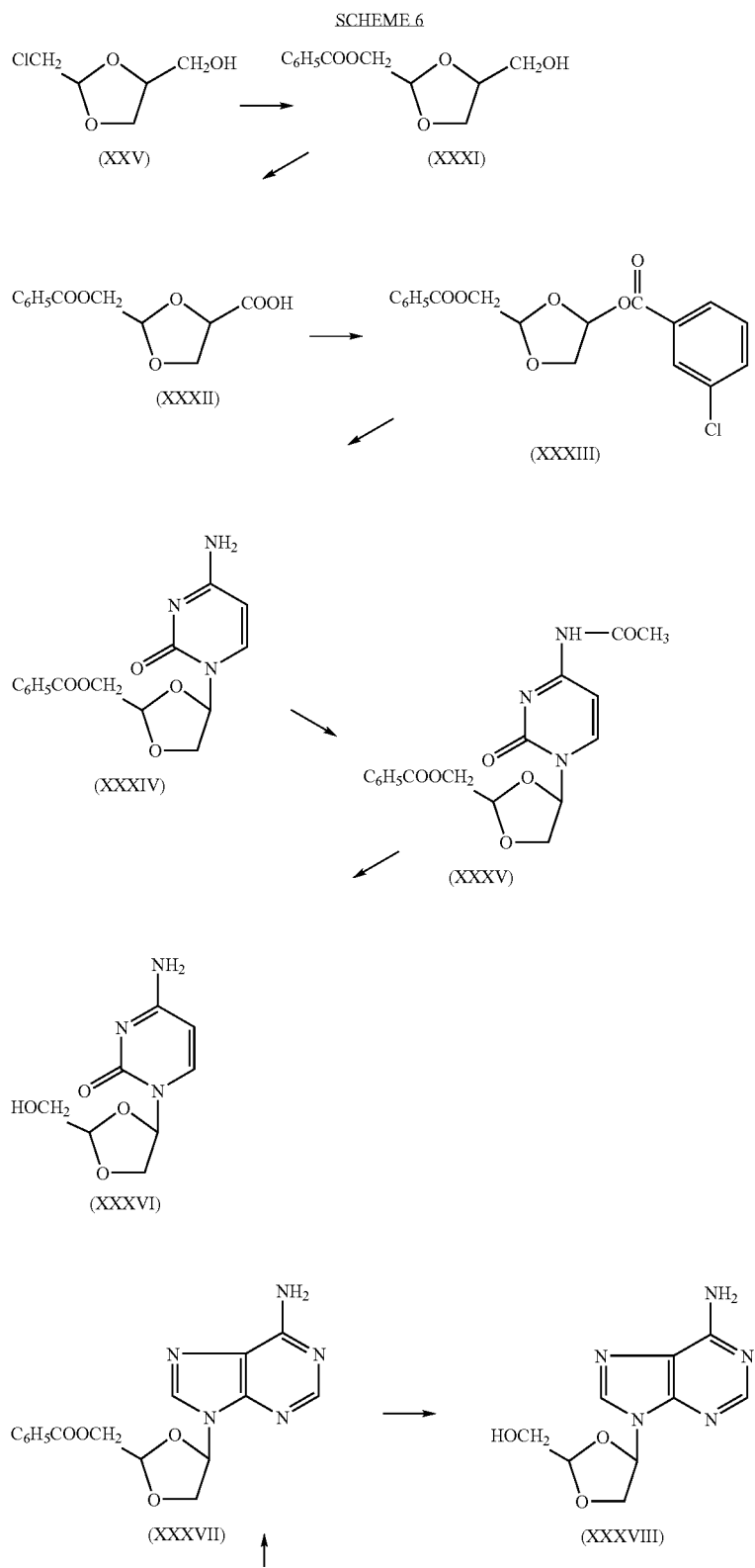
SCHEME 6

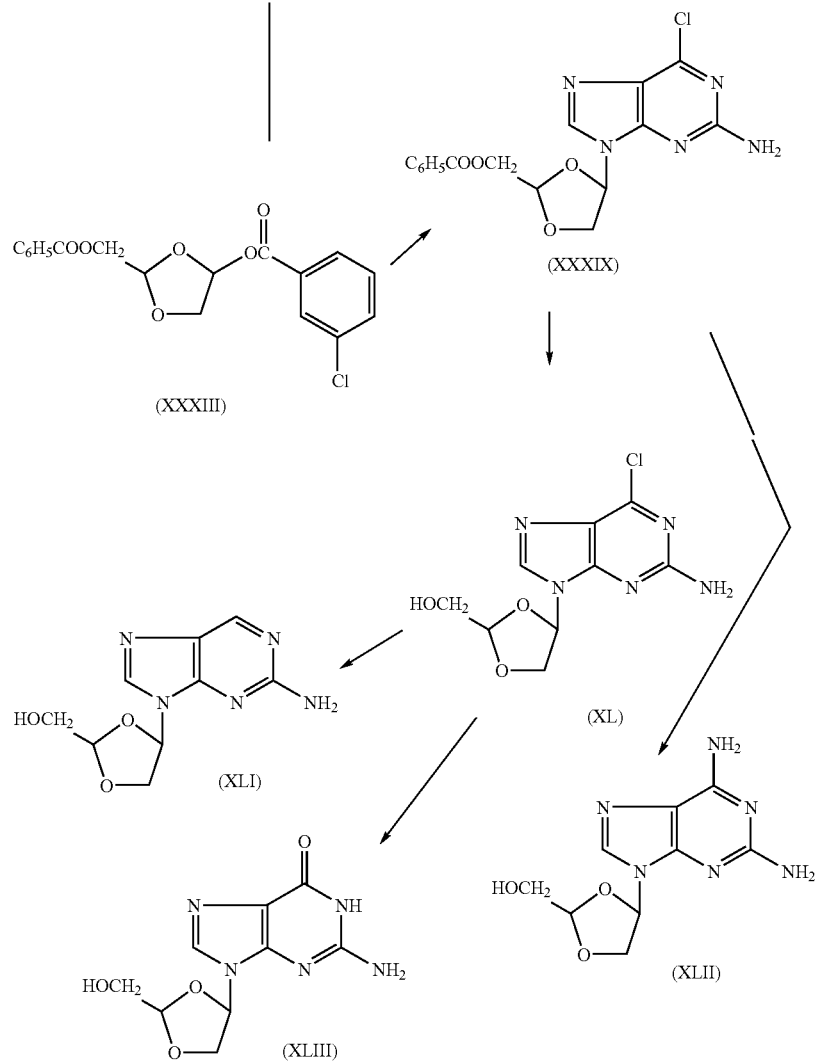
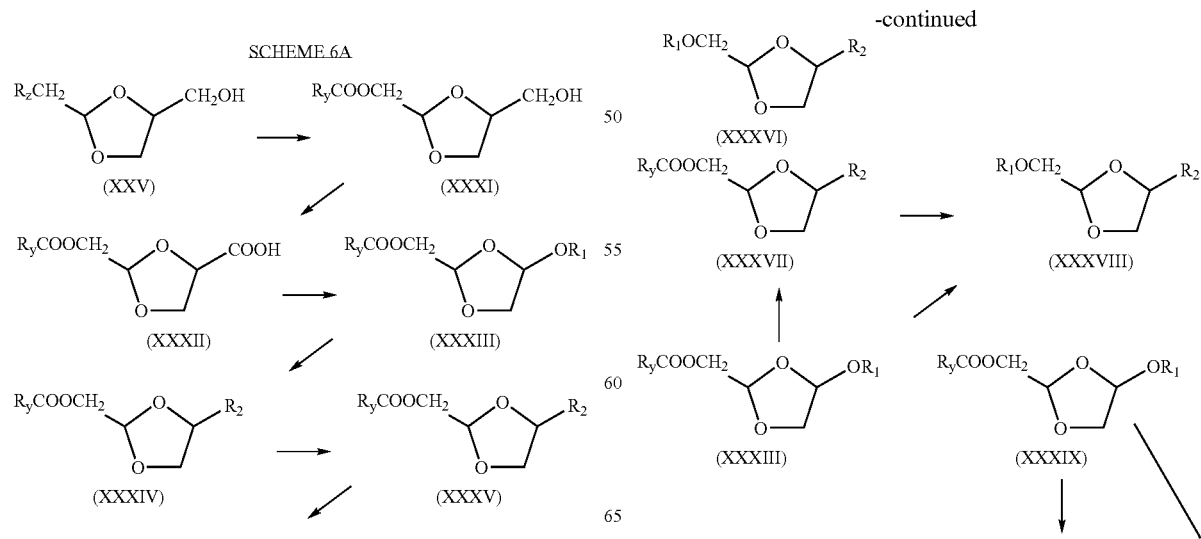
SCHEME 6A

-continued

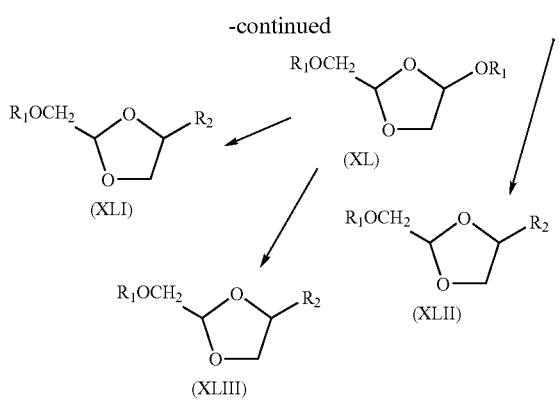

Step 1: The chlorine atom of starting dioxalane of formula (XXV) is displaced by a benzoic (or acetic) acid salt in a solvent such a dimethylformamide to yield the diol monoester of formula (XXXI).

Step 2: The hydroxymethyl group of formula (XXXI) is oxidized with a suitable reagent such as chromic acid (which may be complexed with pyridine) in a compatible organic solvent to give the dioxolane carboxylic acid of formula (XXXII).

Step 3: The acid of formula (XXXII) is then subjected to Bayer-Villiger oxidation by the procedure outlined in Step 2 of SCHEME 5 above to give the corresponding aroyloxy-dioxolane of formula (XXXIII).

Step 4: The intermediate of formula (XXXIII) is reacted with a previously silyated purine or pyrimidine base, such as cytosine, under the reaction conditions outlined in Step 3 of SCHEME 5 to give, e.g., the cytosin-1-yl dioxolane of formula (XXXIV).

Step 5: The amine function of formula (XXXIV) is acylated with acetic anhydride in a solvent such as pyridine to give the compound of formula (XXXV) which provides for easier separation of isomers.

Step 6: The ester and acetyl functions of formula (XXXV) are hydrolyzed under basic conditions to yield the desired end-product of formula (XXXVI).

Step 7: ((XXXIII) to (XXXVII)) The intermediate of formula (XXXIII) is alternatively reacted with a purine or pyrimidine base, such as adenine, by the procedure outlined above in Step 3 of SCHEME 5 to give the compound of formula (XXXVII).

Step 8: ((XXXVII) to (XXXVIII)) The ester function of formula (XXXVII) is hydrolyzed under basic conditions to yield the desired end-product of formula (XXXVIII).

Step 9: ((XXXIII) to (XXXIX)) The intermediate of formula (XXXIII) is alternatively reacted with 2-amino-6-chloropurine under the conditions outlined in Step 3 of SCHEME 5 to give a compound of formula (XXXIX).

Step 10: ((XXXIX) to (XL)) The intermediate (XXXIX) is hydrolyzed under basic conditions to yield the desired end-product of formula (XL).

Step 11: ((XL) to (XLI)) The chlorine atom of formula (XL) is removed by catalytic hydrogenation over Pd/C to give the 2'-amino-purin-9'-yl dioxolane of formula (XLI).

Step 12: The above intermediate (XXXIX) is alternatively reacted with excess ammonia under pressure whereupon the 2',6'-diamino-purin-9'-yl dioxolane of formula (XLII) is produced.

Step 13: The compound of formula (XL) is alternatively subjected to boiling sodium hydroxide to give the desired end-product guanin-9'-yl dioxolane of formula (XLIII).

A third process for preparing dioxolane compounds of the present invention is illustrated in SCHEME 7. Although this process is illustrated using specific reagents and compounds, it will be obvious to one of skill in the art that suitable alternative reactants may be used to prepare analogous products, as depicted, for example, in SCHEME 7A.

The various steps involved in the synthesis illustrated in SCHEME 7 may be briefly described as follows:

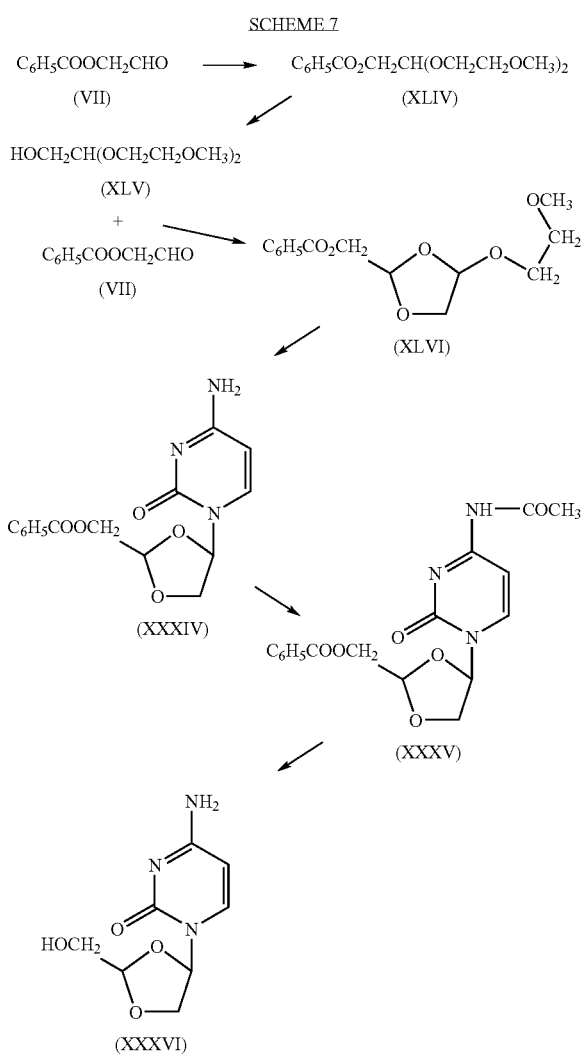

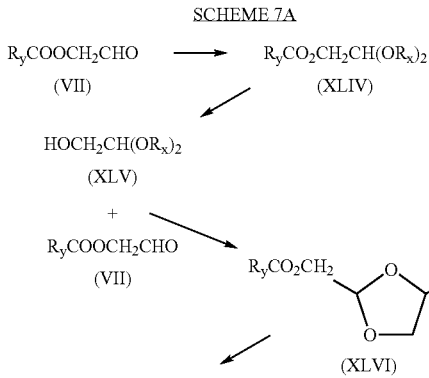

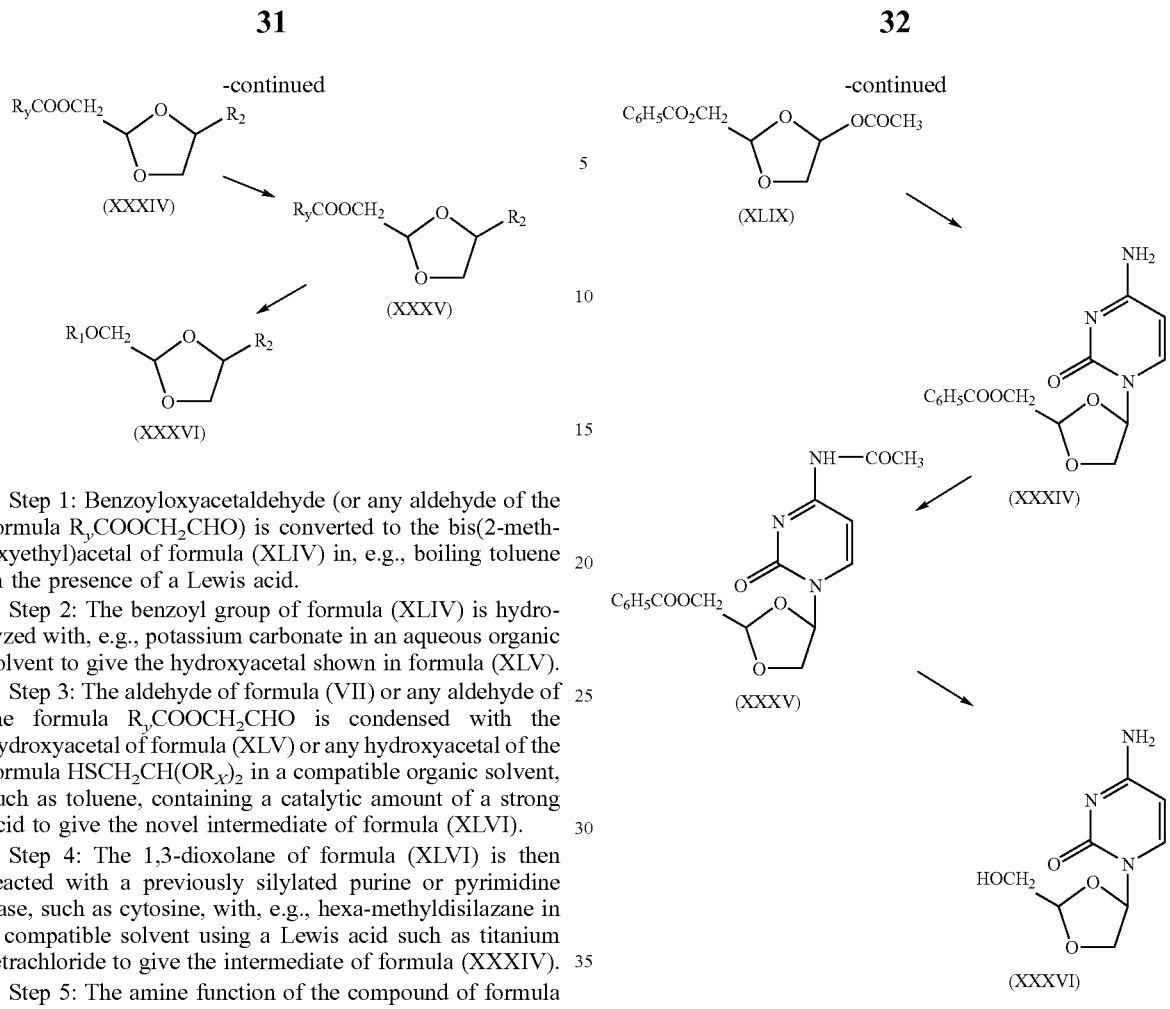

Step 1: Benzoyloxyacetaldehyde (or any aldehyde of the formula $R_yCOOCH_2CHO$) is converted to the bis(2-methoxyethyl)acetal of formula (XLIV) in, e.g., boiling toluene in the presence of a Lewis acid.

Step 2: The benzoyl group of formula (XLIV) is hydrolyzed with, e.g., potassium carbonate in an aqueous organic solvent to give the hydroxyacetal shown in formula (XLV).

Step 3: The aldehyde of formula (VII) or any aldehyde of the formula $R_yCOOCH_2CHO$ is condensed with the hydroxyacetal of formula (XLV) or any hydroxyacetal of the formula $HSCH_2CH(OR_x)_2$ in a compatible organic solvent, such as toluene, containing a catalytic amount of a strong acid to give the novel intermediate of formula (XLVI).

Step 4: The 1,3-dioxolane of formula (XLVI) is then reacted with a previously silylated purine or pyrimidine base, such as cytosine, with, e.g., hexa-methyldisilazane in a compatible solvent using a Lewis acid such as titanium tetrachloride to give the intermediate of formula (XXXIV).

Step 5: The amine function of the compound of formula (XXIV) is acetylated with acetic anhydride to yield the intermediate (XXXV) for easier separation of cis- and trans-isomers.

Step 6: The cis- and/or trans-isomers of formula (XXXV) are treated with, e.g., methanolic ammonia to give the desired product shown in formula (XXXVI) as cis- and trans-isomers.

A preferred process for preparing dioxolane compounds of the present invention is illustrated in SCHEME 8. Although this process is illustrated using specific reagents and compounds, it will be obvious to one of skill in the art that suitable alternative reactants may be used to prepare analogous products, as depicted, for example, in SCHEME 8A.

The various steps involved in the synthesis illustrated in SCHEME 8 may be briefly described as follows:

SCHEME 8

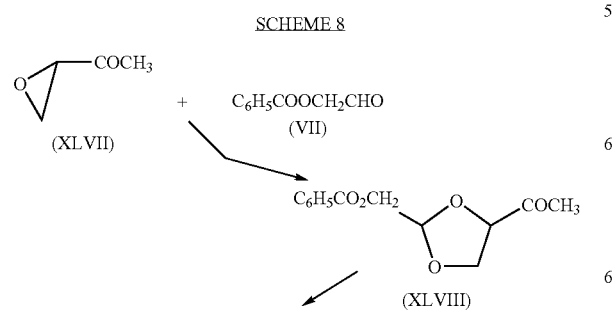

SCHEME 8A

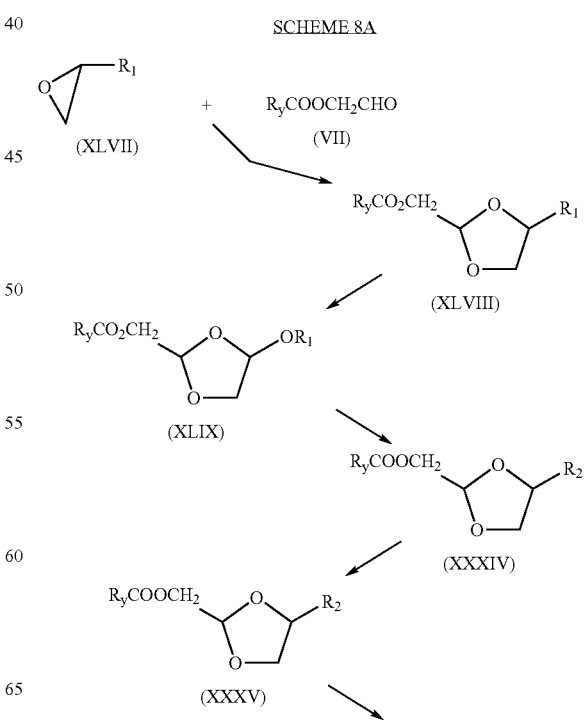

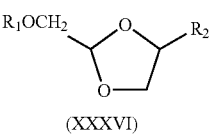

(XXXVI)

Step 1: The aldehyde of formula (VII) or any aldehyde of the formula $R_yCOOCH_2CHO$ is condensed with the known epoxide described in R. L. Wasson and H. O. House, "Preparation of Isophorone Oxide", *Organic Synthesis Collective*, Vol. IV, p. 552 (1963) in an appropriate solvent such as benzene and a suitable Lewis acid such as tetraethylammonium bromide to give dioxolane of formula (XLVIII).

Step 2: The ketone of formula (XLVIII) is subjected to a Bayer-Willinger oxidation with an organic peracid such as m-chloroperbenzoic acid to yield the corresponding acetoxydioxolane (XLIX).

Step 3: The dioxolane of formula (XLIX) is then reacted with a previously silylated purine or pyrimidine base, such as cytosine, with, e.g., hexa-methyldisilazane in a suitable solvent using a Lewis acid or preferrably trimethylsilyl triflate to give the intermediate of formula (XXXIV).

Step 4: The amine function of the compound of formula (XXIV) is acetylated with, e.g., acetic anhydride to yield the intermediate (XXXV) for easier separation of cis- and trans-isomers.

Step 5: The cis- and/or trans-isomers of formula (XXXV) are treated with methanolic ammonia to give the desired product shown in formula (XXXVI) as cis- and trans-isomers.

In the above-identified processes for making the oxathiolane and dioxolane compounds of this invention, the following intermediates are of particular importance:

2-thiobenzoylacetaldehyde diethylacetal (V);
cis- and trans-2-benzoyloxymethyl-5-ethoxy-1,3-oxathiolane (VIII);
cis- and trans-2-benzoyloxymethyl-5-hydroxy-1,3-oxathiolane (XIII);
cis- and trans-2-benzoyloxymethyl-5-acetoxy-1,3-oxathiolane (XIV);
cis- and trans-2-ethoxycarbonyl-5-hydroxy-1,3-oxathiolane (XV);
cis- and trans-2-ethoxycarbonyl-5-acetoxy-1,3-oxathiolane (XVI);
cis- and trans-2-ethoxycarbonyl-5-(uracil-1'-yl)-1,3-oxathiolane (XVII);
cis- and trans-2-t-butyldimethylsilyloxy-methyl-5-(uracil-1'-yl)-1,3-oxathiolane (XIX);
cis- and trans-2-t-butyldimethylsilyloxy-methyl-5-(cytosin-1'-yl)-1,3-oxathiolane (XX);
cis- and trans-2-ethoxycarbonyl-5-(methoxy-carbonyloxy)-1,3-oxathiolane (XXI);
cis- and trans-2-t-butyldiphenylsilyloxy-methyl-5-(methoxycarbonyloxy)-1,3-oxathiolane (XXII);
cis- and trans-2-t-butyldiphenylsilyloxy-methyl-5-(cytosin-1'-yl)-1,3-oxathiolane (XXIII);
cis- and trans-2-t-butyldiphenylsilyloxy-methyl-5-($N_4$-acetylcytosin-1'-yl)-1,3-oxathiolane (XXIV);
cis- and trans-2-chloromethyl-4-(m-chloro-benzoyloxy)-1,3-dioxolane (XXVII);
cis- and trans-2-benzoyloxymethyl-1,3-dioxolane-4-carboxylic acid (XXXII);
cis- and trans-2-benzoyloxymethyl-4-(m-chlorobenzoyloxy)-1,3-dioxolane (XXXIII);
2-benzoyloxyacetaldehyde bis(2-methoxyethyl)acetal (XLIV);
2-hydroxyacetaldehyde bis(2-methoxyethyl)acetal (XLV);
cis- and trans-2-benzoyloxymethyl-4-(2-methoxyethoxy)-1,3-dioxolane (XLVI);
cis- and trans-2-benzoyloxymethyl-4-acetyl-1,3-dioxolane (XLVIII); and
cis- and trans-2-benzoyloxymethyl-4-acetoxy-1,3-dioxolane (XLIX).

In addition, the following intermediates, although not specifically depicted in the above identified processes, are important intermediates for making the oxathiolane and dioxolane compounds of this invention:
2-thiobenzoylacetaldehyde bis(2-methoxyethyl)acetal;
2-thioacetaldehyde bis(2-methoxyethyl acetal;
cis- and trans-2-benzoyloxymethyl-5-(2-methoxyethoxy)-1,3-oxathiolane.
cis- and trans-2-hydroxymethyl-5-hydroxy-1,3-oxathiolane; and
cis- and trans-2-acetoxymethyl-5-1,3-oxathiolane.

Many of the reactions described hereinabove have been extensively reported in the context of purine nucleoside synthesis, for example, in "Nucleoside Analogues—Chemistry, Biology and Medical Applications", R. T. Walker et al., Eds, Plenum Press, New York (1979) at pages 193–223, the text of which is incorporated by reference herein.

As used in the processes of this invention, a "leaving group" is an atom or group which is displaceable upon reaction with an appropriate base, with or without a Lewis acid. Suitable leaving groups include alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated selenino compounds, such as phenyl selenide or alkyl selenide; substituted or unsubstituted, saturated or unsaturated aliphatic or aromatic ketones such as methyl ketone; or —OR where R is a substituted or unsubstituted, saturated or unsaturated alkyl group, e.g., $C_{1-6}$ alkyl or alkenyl group; a substituted or unsubstituted aliphatic or aromatic acyl group, e.g., a $C_{1-6}$ aliphatic acyl group such as acetyl and an aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidate group such as trichloroacetamidate; substituted or unsubstituted, saturated or unsaturated phosphonates, such as diethylphosphonate; substituted or unsubstituted aliphatic or aromatic sulphonyl group, such as tosylate; or hydrogen.

It will be appreciated that the reactions of the above-described processes may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g., benzyl), acyl or aryl (e.g., 2,4-dinitrophenyl); subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981). Examples of suitable hydroxyl protecting groups include groups selected from alkyl (e.g., methyl, t-butyl or methoxymethyl), aralkyl (e.g., benzyl, diphenylmethyl or triphenylmethyl), heterocyclic groups such as tetrahydropyranyl, acyl, (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may similarly be removed by solvolysis, e.g., by hydrolysis under acidic conditions. Aralkyl groups such as benzyl may be cleaved, for example, by treatment with $BF_3$/etherate and acetic anhydride followed by removal of acetate groups so formed at an appropriate stage in the synthesis. Silyl groups may also conveniently be removed using a source of fluoride ions such as tetra-n-butylammonium fluoride.

In the above processes the compounds of formula (I) are generally obtained as a mixture of the cis and trans isomers.

These isomers may be separated, for example, by acetylation, e.g., with acetic anhydride followed by separation by physical means, e.g., chromatography on silica gel and deacetylation, e.g., with methanolic ammonia or by fractional crystallization.

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of a compound of formula (I), the product of any of the above procedures may be converted into a salt by treatment of the resulting free base with a suitable acid using conventional methods. Pharmaceutically acceptable acid addition salts may be prepared by reacting the free base with an appropriate acid optionally in the presence of a suitable solvent such as an ester (e.g., ethyl acetate) or an alcohol (e.g., methanol, ethanol or isopropanol). Inorganic basic salts may be prepared by reacting the free base with a suitable base such as an alkoxide (e.g., sodium methoxide) optionally in the presence of a solvent such as an alcohol (e.g., methanol). Pharmaceutically acceptable salts may also be prepared from other salts, including other pharmaceutically acceptable salts, of the compounds of formula (I) using conventional methods.

A compound of formula (I) may be converted into a pharmaceutically acceptable phosphate or other ester by reaction with a phosphorylating agent, such as $POCl_3$, or a suitable esterifying agent, such as an acid halide or anhydride, as appropriate. An ester or salt of a compound of formula (I) may be converted to the parent compound, for example, by hydrolysis.

Where the compound of formula (I) is desired as a single isomer it may be obtained either by resolution of the final product or by stereospecific synthesis from isomerically pure starting material or any convenient intermediate.

Resolution of the final product, or an intermediate or starting material therefore may be effected by any suitable method known in the art: see for example, *Stereochemistry of Carbon Compounds*, by E. L. Eliel (McGraw Hill, 1962) and *Tables of Resolving Agents*, by S. H. Wilen.

The invention will be further described by the following examples which are not intended to limit the invention in any way. All temperatures are in degrees celsius.

EXAMPLES

Example 1

2-thiobenzoyl acetaldehyde diethylacetal

$C_6H_5COS\text{---}CH_2CH(OC_2H_5)_2$ (V)

To a solution of potassium t-butoxide (11.5 g. 0.11 mol) in DMF (100 ml) was added thioben-zoic acid (17 g. 0.11 mol) and the solution partially evaporated in vacuo, benzene added in two consecutive portions (2×30 ml) and evaporated in vacuo each time. To the residual DMF solution was added bromoacetaldehyde diethylacetal (20.3 g. 0.1 mol) and the mixture stirred at 120° for 15 h. After cooling, it was poured onto water (500 ml), the product extracted with ether (3×200 ml), the extract washed with aqueous $NaHCO_3$ followed by water, then dried and the solvent removed in vacuo. The residue was distilled in vacuo to give 17.2 g. of pure (V), b.p. 131–133°/0.07 mm. It was characterized by $^1H$ NMR δ(ppm in $CDCl_3$):
7.97 (d, 2H; aromatic)
7.47 (m, 3H; aromatic)
4.59 (t, 1H; —C$\underline{H}$(O$C_2H_5$)$_2$))
3.66 (m, 4H; 2×OC$\underline{H}_2$C$H_3$)
3.30 (d, 2H; SC$\underline{H}_2$—)
1.23 (t, 6H; 2×OC$H_2$C$\underline{H}_3$)

Example 2

Mercaptoacetaldehyde diethylacetal

$HSCH_2CH(OC_2H_5)_2$ (VI)

The preceding thiobenzoyl derivative (v) (17.2 g) was dissolved in 100 ml THF followed by the addition of 6 g NaOH in 20 ml $H_2O$. The mixture was refluxed under $N_2$ for 15 h, then cooled and diluted with water (200 ml) and the product extracted with ether (3×200 ml). The extract was dried, the solvent removed in vacuo and the residue distilled in vacuo to yield 7.1 g of pure (VI), b.p. 60–62°/18 mm. It was characterized by $^1H$ NMR δ(ppm in $CDCl_3$):
4.51 (t, 1H; C$\underline{H}$(O$C_2H_5$)$_2$)
3.51 (m, 4H; 2×OC$\underline{H}_2$C$H_3$)
2.65 (dd, 2H; HS—C$\underline{H}_2$)
1.54 (t, 1H; $\underline{H}$S—)
1.23 (t, 6H; 2×OC$H_2$C$\underline{H}_3$)

Example 3

Benzoyloxyacetaldehyde

$C_6H_5COOCH_2CHO$ (VII)

This known intermediate was prepared by a previously unreported method from the known 1-benzoyl glycerol. Thus, 50 g of the latter in a mixture of 500 ml of $CH_2Cl_2$ and 25 ml of $H_2O$ was treated portion-wise with 80 g of $NaIO_4$ under vigorous stirring at room temperature. After addition, stirring was continued for 2 h after which time 100 g of $MgSO_4$ was added and stirring continued for 30 min. The mixture was filtered, the filtrate evaporated in vacuo and the residue distilled in vacuo to yield 26 g of pure (VII) b.p. 92–94°/0.25 mm. $^1H$ NMR (200 M$H_z$; TMS as internal reference)
δ(ppm in $CDCl_3$'):
9.71 (s, 1H; —C$\underline{H}$O)

8.11 (d, 2H; aromatic)
7.60 (m, 1H; aromatic)
7.46 (m, 2H; aromatic)
4.88 (s, 2H; —C$\underline{H}_2$CHO)

Example 4

2-Benzoyloxymethyl-5-ethoxy-1,3-oxathiolane

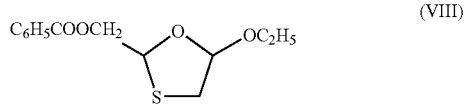
(VIII)

The preceding mercaptoacetaldehyde acetal (VI) (7 g) was mixed in 100 ml of toluene with 7 g of the above benzoyloxyacetaldehyde (VII), a few crystals of para-toluene sulfonic acid added and the mixture placed in an oil-bath at 120° under N$_2$. The formed ethanol was allowed to distill over, the mixture kept at 120° for an additional 30 minutes, then cooled and washed with aqueous NaHCO$_3$, dried and evaporated in vacuo. The residue was distilled in vacuo to yield 9.8 g of pure (VIII) as a mixture of cis- and trans-isomers, b.p. 140–143°/0.1 mm; R$_f$ 0.51 (hexane-EtoAc);
$^1$H NMR δ(ppm in CDCl$_3$):
8.05 (m, 2H; aromatic)
7.57 (m, 1H; aromatic)
7.43 (m, 2H; aromatic)
5.55 (m, 2H; C$_5$—$\underline{H}$, C$_2$—$\underline{H}$)
4.55 (m, 2H; C$_2$—C$_6$H$_5$CO$_2$C$\underline{H}_2$)
3.80 (m, 1H; C$_5$—OC$\underline{H}$CH$_3$)
3.76 (m, 1H; C$_5$—OC$\underline{H}$CH$_3$)
3.17 (m, 2H; C$_4$—$\underline{H}_2$)
1.21 (t, 3H; C$_5$—OCH$_2$C$\underline{H}_3$)

Example 5

Cis- and trans-2-benzoyloxymethyl-5-(cytosin-1'-yl)-1,3-oxathiolane

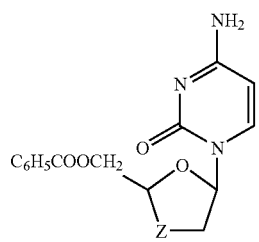
(IX)

A mixture of 2.7 g of cytosine, 30 ml of hexamethyldisilazane (HMDS) and 0.3 ml of trimethylsilyl chloride (TM-SCl) was heated under reflux under dry N$_2$ until a clear solution resulted (3 hours) and the excess reagents evaporated in vacuo. The remaining volatiles were removed under high vacuum (15 min.), the solid residue taken up in 250 ml of 1,2-dichloroethane and 5 g of the above intermediate (VIII) in 50 ml of dichloroethane added under dry argon followed by 4.7 ml of trimethylsilyl triflate (TMST$_f$). After 3 days of heating under reflux under argon, it was cooled and poured onto 300 ml of saturated aqueous NaHCO$_3$. The organic layer was collected, the aqueous phase extracted with CH$_2$Cl$_2$ (2×100 ml) and the combined extracts washed with water, dried and evaporated in vacuo. The residue was purified by chromatography on silica gel using CH$_2$Cl$_2$:CH$_3$OH 9:1 as the eluant to give 2.5 g of a pure mixture of cis- and trans-(IX) in a 1:1 ratio as ascertained by $^1$H NMR. These were separated as the N-acetyl derivatives as described in the following example.

Example 6

Cis- and trans-isomers of 2-benzoyloxymethyl-5-(N$_4$'-acetyl-cytosin-1'-yl)-1,3-oxathiolane

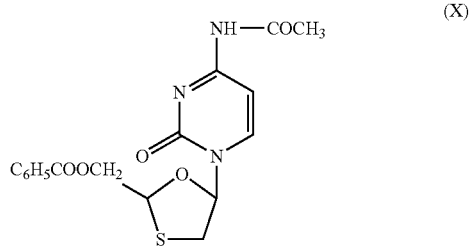
(X)

The preceding mixture (IX) (2.5 g) in 100 ml of dry pyridine containing 0.1 g of 4-dimethylamino-pyridine (DMAP) was treated with acetic anhydride (7 ml) at room temperature and after 16 hours, the mixture was poured onto cold water followed by extraction with CH$_2$Cl$_2$ (3×150 ml). The extract was washed with water, dried, and evaporated in vacuo. Toluene was added to the residue, then evaporated in vacuo and the residual oil purified by chromatography on silica gel using EtOAc:CH$_3$OH 99:1 as the eluant to yield 1.35 g of pure trans-(X) as the fast moving product and 1.20 g of pure cis-(X) as the slow moving component. These were characterized by $^1$H NMR spectroscopy.

trans-(X): m.p. 158–160°; R$_f$: 0.48 EtOAc:CH$_3$OH 95:5
U.V.: (CH$_3$OH) Lambda max: 297 nm
$^1$H NMR δ(ppm in CDCl$_3$):
9.00 (b, 1H; C$_4$'—N$\underline{H}$—Ac)
8.06 (m, 2H; aromatic)
7.74 (d, 1H; C$_6$'—$\underline{H}$)
7.56 (m, 1H; aromatic)
7.47 (d, 1H; C$_5$'—$\underline{H}$)
7.45 (m, 2H; aromatic)
6.53 (dd, 1H; C$_5$—$\underline{H}$)
5.89 (dd, 1H; C$_2$—$\underline{H}$)
4.46 (dd, 2H; C$_2$—C$\underline{H}_2$OCOC$_6$H$_5$)
3.66 (dd, 1H; C$_4$—H)
3.32 (dd, 1H; C$_4$—H)
2.25 (s, 3H; NH—COC$\underline{H}_3$)
Cis-(X): m.p. 150–152°; R$_f$: 0.40 EtOAc:MeOH 95:5)
U.V.: (CH$_3$OH) Lambda max: 297 nm
$^1$H NMR δ(ppm in CDCl$_3$):
9.03 (b, 1H; N$\underline{H}$—Ac)
8.21 (d, 1H; C$_6$'—$\underline{H}$)
8.05 (m, 2H; aromatic)
7.60 (m, 1H; aromatic)
7.50 (m, 2H; aromatic)
7.29 (d, 1H; C$_5$'—$\underline{H}$)
6.34 (dd, 1H; C$_5$—$\underline{H}$)
5.52 (dd, 1H; C$_2$—$\underline{H}$)
4.80 (dd, 2H; C$_2$—C$\underline{H}_2$OCOC$_6$H$_5$)

3.66 (dd, 1H; C$_4$—H)
3.24 (dd, 1H; C$_4$—H)
2.23 (s, 3H; NH—COCH$_3$)

Example 7

Cis- and trans-2-hydroxymethyl-5-(cytosin-1'-yl)-1,3-oxathiolane

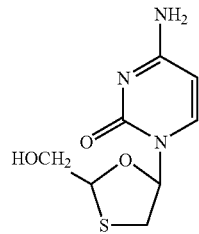
(XI)

a) Trans-(XI): 375 mg of the preceding trans-(X) was dissolved in 100 ml of methanolic ammonia at 24° and after stirring for 16 hours, the solvent was removed in vacuo and the residue crystallized with ether. It was recrystallized from ethanol-ether to yield 174 mg of pure product, m.p. >220° (dec). It was characterized by 1H and $^{13}$C NMR.

$^1$H NMR δ(ppm in DMSO-d$_6$):
7.57 (d, 1H; C$_6$'—H)
7.18 (d, 2H; C$_4$'—NH$_2$)
6.30 (dd, 1H; C$_5$—H)
5.68 (d, 1H; C$_5$'—H)
5.48 (t, 1H; C$_2$—H)
5.18 (t, 1H; C$_2$—CH$_2$OH)
3.45 (m, 3H; C$_2$—CH$_2$OH+C$_4$H)
3.06 (dd, 1H; C$_4$—H)
U.V.: (CH$_3$OH) Lambda max: 270 nm
$^{13}$C NMR (DMSO-d$_6$, Varian XL-300); δ in ppm:

| C$_2$' | C$_4$' | C$_5$' | C$_6$' | C$_5$ | C$_4$ | C$_2$ | CH$_2$OH |
|---|---|---|---|---|---|---|---|
| 154.71 | 165.70 | 93.47 | 140.95 | 87.77 | 36.14 | 86.80 | 64.71 | b) Cis-(XI): treating 375 mg of cis-(X) by the same preceding procedure led to 165 mg of pure product after recrystallization from ethanol-ether, m.p. 171–173°. It was characterized by $^1$H and $^{13}$C NMR.

$^1$H NMR: δ(ppm in DMSO-d$_6$):
7.80 (d, 1H; C$_6$—H)
7.20 (d, 2H; C$_4$'—NH$_2$)
6.18 (t, 1H; C$_5$—H)
5.70 (d, 1H; C$_5$'—H)
5.14 (t, 1H; C$_2$—CH$_2$OH)
3.71 (m, 2H; C$_2$—CH$_2$OH)
3.40 (dd, 1H; C$_4$—H)
2.99 (dd, 1H; C$_4$—H).
U.V.: (CH$_3$OH) Lambda max: 270 nm
$^{13}$C NMR δ (ppm in DMSO-d$_6$)

| C$_2$' | C$_4$' | C$_5$' | C$_6$' | C$_5$ | C$_4$ | C$_2$ | CH$_2$OH |
|---|---|---|---|---|---|---|---|
| 154.63 | 165.59 | 93.86 | 140.91 | 86.47 | 36.22 | 85.75 | 62.79 |

Example 8

Cis-2-hydroxymethyl-5-(cytosin-1'-yl)-3-oxo-1,3-oxathiolane

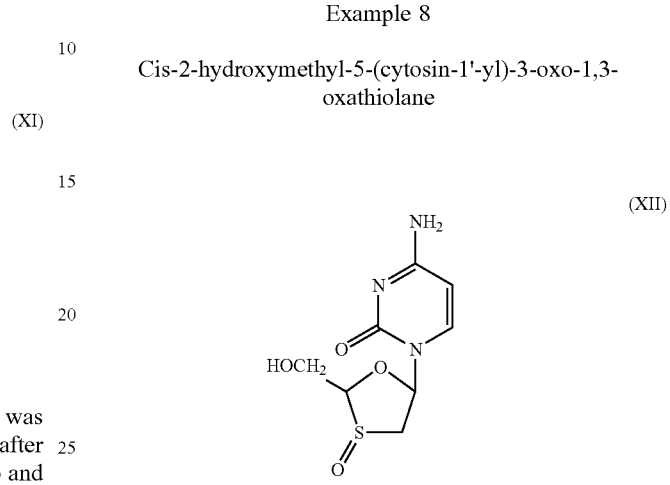
(XII)

The preceding cis-(XI) (100 mg) in 30 ml of ice-cold methanol was treated with 93 mg of meta-chloroperbenzoic acid and after stirring for 15 min a white solid separated which was collected and washed with 10 ml of methanol to give 45 mg of pure sulfoxide isomer a. The methanol filtrates were evaporated in vacuo and the solid residue washed with 15 ml of ethanolether (1:1) and then with 30 ml of ether to give 50 mg of pure sulfoxide isomer b. The isomers were characterized by $^1$H NMR.

Isomer (XII)a: m.p.>270° (dec); R$_f$: 0.30 (CH$_2$Cl$_2$—MeOH 3:1)
U.V.: (CH$_3$OH) Lambda max: 270 nm
$^1$H NMR δ (ppm in DMSO-d$_6$):
7.68 (d, 1H; C$_6$'—H)
7.36 (s, 2H; C$_4$'—NH$_2$)
6.69 (dd, 1H; C$_5$—H)
5.76 (d, 1H; C$_5$'—H)
5.47 (t, 1H; C$_2$—CH$_2$OH)
4.63 (dd 1H; C$_2$—H)
3.88 (m, 1H; C$_2$—CH—OH)
3.72 (m, 1H; C$_2$—CH—OH)
3.36 (dd, 1H; C$_4$—H)
3.05 (dd, 1H; C$_4$—H)
Isomer (XII)b: m.p.>220° (dec); R$_f$: 0.32 CH$_2$Cl$_2$:MeOH 3:1 $^1$H NMR δ (ppm in DMSO-d$_6$):
7.76 (d, 1H; C$_6$'—H)
7.28 (d, 2H; C$_4$'—NH$_2$)
6.66 (dd, 1H; C$_5$—H)
5.77 (d, 1H; C$_5$'—H)
5.45 (t, 1H; C$_2$—CH$_2$OH)
4.64 (t, 1H; C$_2$—H)
3.77 (t, 2H; C$_2$—CH$_2$OH)
3.65 (dd, 1H; C$_4$—H)
3.17 (dd, 1H; C$_4$—H)

Example 9

Cis-2-hydroxymethyl-5-(N-dimethylamino methylene cytosin-1'-yl)-1,3-oxathiolane

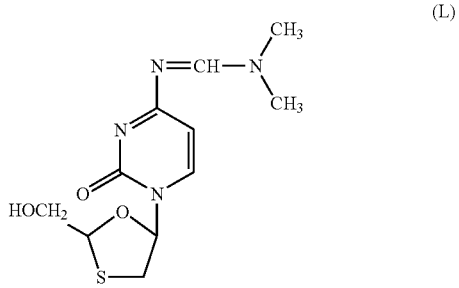
(L)

300 mg of cis-2-hydroxymethyl-5-(cytosin-1'-yl) 1,3-oxathiolane was suspended in 10 ml of N-dimethylformamide dimethyl acetal (DMF-dimethyl acetal). The mixture was stirred at room temperature overnight (18 hours). Volatile material was removed by evaporation under reduced pressure. The residue was crystallized in ethanol-ether. It yielded 345 mg (93%) of pure product. m.p. 162–164° C.; $R_f$: 0.56 in $CH_2Cl_2$:MeOH 4:1

U.V.: Lambda max: 325 nm
$^1$H NMR δ(ppm in DMSO-$d_6$):
8.64 (s, 1H, N═CH—N)
8.04 (d, 1H, $C_6'$—H, J=7.2 Hz)
6.22 (t, 1H, $C_5$—H, J=4.9 Hz)
5.97 (d, 1H, $C_5'$—H, J=7.2 Hz)
5.37 (t, 1H, —OH, J=5.8 Hz, $D_2O$ exchange)
5.22 (t, 1H, $C_2$—H, J=4.4 Hz)
3.77 (t, 2H, $C_2$—$CH_2$OH, J=4.9 Hz)
3.50 (dd, 1H, $C_4$—H, J=4.9 and 9.9 Hz)
3.17 (s, 3H, —$CH_3$)
3.12 (dd, 1H, $C_4$—H, J=4.2 and 11.9 Hz)
3.04 (s, 3H, —$CH_3$)

Example 10

Bis-Cis-2-succinyloxymethyl-5-(cytosin-1'-yl)-1,3-oxathiolane

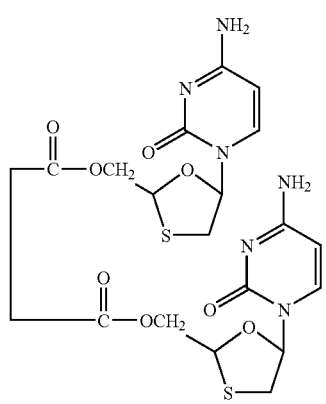
(LI)

284 mg of cis-2-hydroxymethyl-5-(N,N-dimethylamino methylene cytosin-1'-yl)-1,3-oxathiolane was dissolved in 10 ml of dry pyridine and cooled at 0° C. in an ice-bath. 60 μl of succinyl chloride was added via a syringe. The mixture was stirred overnight (18 hours) and poured into 50 ml of saturated aqueous $NaHCO_3$ solution. The mixture was extracted with methylene chloride (3×50 ml). The combined $CH_2Cl_2$ solution was washed with water (2×50 ml) and dried over $MgSO_4$. After filtration, solvent was removed by evaporation under reduced pressure. The foam residue was dissolved in 10 ml of $CH_2Cl_2$ containing 5 ml of methanol. 2 ml of 80% aqueous acetic acid was added and the mixture was stirred at room temperature overnight. The mixture was evaporated to dryness. The solid residue was purified on silica gel using $CH_2Cl_2$: MeOH 4:1 as eluant. It yielded 145 mg (54%) of pure product.

m.p. Dec >230° C.; $R_f$: 0.23 (in $CH_2Cl_2$:MeOH 4:1)
U.V.: (MeOH) Lambda max: 271 nm
$^1$H-NMR δ(ppm in DMSO-$d_6$)
7.69 (d, 2H, 2×$C_6'$—H, J=7.6 Hz)
7.28 (d, 4H, 2×$NH_2$, J=24.9 Hz, $D_2O$ exchange)
6.24 (t, 2H, 2×$C_5$—H, J=5.6 Hz)
5.76 (d, 2H, 2×$C_5'$—H; J=7.4 Hz)
5.35 (t, 2H, 2×$C_2$—H, J=4.5 Hz)
4.37 (d, 4H, 2×$C_2$—$CH_2$O—)
3.42 (dd, 2H, 2×$C_4$—H, J=5.5 and 10.9 Hz)
3.10 (dd, 2H, 2×$C_4$—H, J=5.6 and 11.7 Hz)
2.60 (s, 4H, 2×—$CH_2$—C—O)

Example 11

Cis- and trans-2-benzoyloxymethyl-5-(6'-chloropurin-N-9'-yl)-1,3-oxathiolane

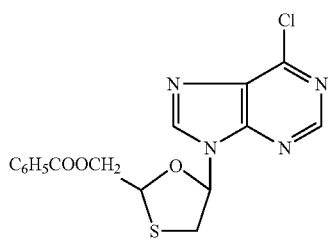
(LII)

1.7 g of 6-chloropurine was heated at reflux in 50 ml of HMDS (hexamethyldisilazane) containing 50 mg of $(NH_4)_2SO_4$(ammonium sulfate) until the solution became clear (1 hour). Excess HMDS was removed under reduced pressure. The oily residue was dried under high vacuum for 1 hour and then dissolved in 100 ml of dry 1,2-dichloroethane.

2.7 g of 2-benzoyloxymethyl-5-ethoxy-1,3-oxathiolane (VIII) was dried in a 500 ml round bottom flask by evaporation twice with 50 ml of benzene and dissolved in 200 ml of dry 1,2-dichloroethane.

The solution of silylated 6-chloropurine was then transferred into the 1,3-oxathiolane solution through a canula under argon atmosphere. 11 ml of 1M TMS-triflate (trimethylsilyl trifluoromethane sulfonate) was added to the reaction flask. The mixture was heated at reflux for 5 hours, then cooled to room temperature. The mixture was poured into 300 ml of saturated sodium bicarbonate solution ($NaHCO_3$ solution) while stirring. The organic layer was collected and the aqueous phase was extracted with $CH_2Cl_2$ (2×100 ml). The combined organic phase was washed with water, dried over $MgSO_{4}$, filtered and evaporated under reduced pressure. The residue was purified and separated on silica gel using Hexane-ethyl acetate 7:3 as eluant. It yielded 1.05 g (28%) of the less polar product, which was identified as alpha- or trans-isomer as a foam, and 710 mg of lower product as beta- or cis-isomer. Total yield 46.1%; cis:trans ratio 1:1.4 trans-isomer (α-isomer): $R_f$: 0.43 in Hexane:EtOAc 1:1
U.V.: (MeOH) Lambda max: 264.7 nm
$^1$H-NMR δ(ppm in CDCl$_3$):
8.76 (s, 1H, C$_8$'—H)
8.48 (s, 1H, C$_2$'—H)
8.06 (m, 2H, aromatic)
7.56 (m, 1H, aromatic)
7.45 (m, 2H, aromatic)
6.90 (dd, 1H, C$_5$—H, J=5.0 Hz)
5.78 (dd, 1H, C$_2$—H, J=6.0 Hz)
4.56 (m, 2H, C$_2$—CH$_2$OCOC$_6$H$_5$)
3.74 (m, 2H, C$_4$—H)

cis-isomer (beta-isomer): $R_f$: 0:35 in Hexane:EtOAc: 1:1
U.V.: (MeOH) Lambda max 264.7 nm
$^1$H-NMR δ(ppm in CDCl$_3$):
8.72 (s, 1H, C$_8$'—H)
8.51 (s, 1H, C$_2$'—H)
8.00 (m, 2H, aromatic)
7.56 (m, 1H, aromatic)
7.44 (m, 2H, aromatic)
6.61 (t, 1H, C$_5$—H, J=4.7 Hz)
5.62 (t, 1H, C$_2$—H, J=4.9 Hz)
4.69 (m, 2H, C$_2$—CH$_2$OCOC$_6$H$_5$)
3.66 (m, 2H, C$_4$—H)

Example 12

Cis-2-hydroxymethyl-5-(6'-hydroxypurin-N-9'-yl)-1,3-oxathiolane (inosine derivative)

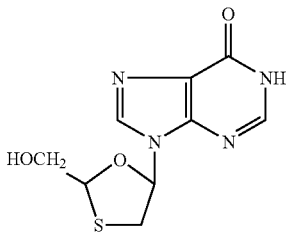

(LIII)

533 mg of cis-2-benzoyloxymethyl-5-(6-chloropurin-N-9'-yl)-1,3-oxathiolane was dissolved in 25 ml of methanol. 5 g of sodium hydroxide (NaOH) and 3 ml of water were added into the solution. The mixture was heated at reflux for 5 hours and cooled to room temperature. The solution was then diluted with 100 ml of water, neutralized with pyridinium resin and filtered. The resin residue was washed with 100 ml of methanol. The combined filtrate was evaporated under reduced pressure. The residue was purified on silica gel using CH$_2$Cl$_2$:MeOH 4:1 as eluant. It yielded 183 mg (51%) of pure product, which was identified as inosine derivative.

m.p.: 208–210° C.; $R_f$: 0.27 in EtOAc:MeOH 4:1
U.V.: (MeOH) Lambda max: 246 nm
$^1$H-NMR: δ(ppm in DMSO-d$_6$)
12.42 (s, 1H, —NH, D$_2$O exchange)
8.36 (s, 1H, C$_8$'—H)
8.07 (s, 1H, C$_2$'—H)
6.37 (t, 1H, C$_5$—H, J=5.1 Hz)
5.29 (t, 1H, —OH, J=6.0 Hz, D$_2$O exchange)
5.24 (t, 1H, C$_2$—H, J=4.9 Hz)
3.63 (m, 4H, 2H from C$_4$—H and 2H from CH$_2$—OH)

Example 13

Cis- and trans-2-benzoyloxymethyl-5-(uracil-N-1'-yl)-1,3-oxathiolane

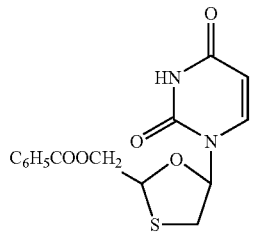

(LIV)

760 mg of uracil was heated at reflux in 30 ml of HMDS in the presence of 50 mg (NH$_4$)$_2$SO$_4$ until the solution became clear. The mixture was evaporated under reduced pressure. The residue was dried under high vacuum for 1 hour and dissolved in 100 ml of dry 1,2-dichloroethane.

1.5 g of 2-benzoyloxymethyl-5-ethoxy-1,3-oxathiolane was dried by evaporation twice with 50 ml of benzene in a 500 ml round bottom flask and dissolved in 150 ml of dry 1,2-dichloroethane.

The silyated uracil solution was transferred into the oxathiolane solution through a canula under argon atmosphere and 1.5 ml of TMS-Triflate in 20 ml of 1,2-dichloroethane was added. The reaction mixture was heated at reflux under argon atmosphere for 48 hours, cooled to room temperature and poured into 300 ml of saturated aqueous NaHCO$_3$ solution. The organic layer was collected. The aqueous phase was extracted twice with CH$_2$Cl$_2$ (2×100 ml). The combined organic layer was washed with water (2×200 ml), once with NaCl solution (1×150 ml) and dried over MgSO$_4$. After filtration, solvent was removed by evaporation in vacuum and the residue was purified on silica gel using Hexane:EtOAc 1:1 as eluant. It yielded 594 mg (32%) of pure product.

The product was shown as only one spot in the TLC. However the $^1$H-NMR spectrum indicated the presence of two isomers cis:trans in a ratio of 1:1.2 and which were not separated at this stage.

$R_f$: 0.35 in Hexane:EtoAc 3:7
U.V.: (MeOH) Lambda max: 261 nm
$^1$H-NMR δ(ppm in CDCl$_3$)
8.88 (broad s, 1H, N$_3$'—H)
8.05 (m, 2H, aromatic)
7.71 (d, 1H, C$_6$'—H cis, J=8.2 Hz)
7.57 (m, 1H, aromatic)
7.45 (m, 3H, aromatic and N$_3$'—H)
6.55 (dd, 1H, C$_5$—H trans, J=2.4 and 5.4 Hz)
6.35 (dd, 1H, C$_5$—H cis, J 4.1 and 5.6 Hz)
5.79 (t, 1H, C$_2$—H trans, J=5.4 Hz)
5.73 (d, 1H, C$_5$'—H trans, J=8.2 Hz)
5.57 (d, 1H, C$_5$'—H cis, J=8.2 Hz)
5.46 (t, 1H, C$_2$—H cis, J=3.9 Hz)
4.73 (d, 2H, —CH$_2$O—COC$_6$H$_5$)
4.45 (t, 2H, —CH$_2$OCOC$_6$H$_5$)
3.57 (m, 1H, C$_4$—H)
3.17 (m, 1H, C$_4$—H)

Example 14

Cis-2-hydroxymethyl-5-(uracil-N-1'-yl)-1,3-oxathiolane

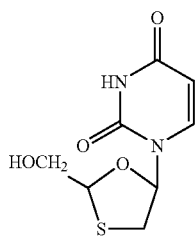

(XVIII)

300 mg of a mixture cis- and trans-2-benzoyloxymethyl-5-(uracil-N-1'-yl)-1,3-oxathiolanes was dissolved in 75 ml of methanolic ammonia. The mixture was stirred at room temperature overnight. The solution was evaporated by dryness. The residue was purified and the two isomers were separated on silica gel using EtOAc:MeOH 98:2 as eluant.

The top product was isolated as a solid product and was identified as cis-isomer.

Cis-isomer: m.p. 162–164° C.; $R_f$: 0.57 in EtoAc:MeOH 95:5

U.V.: (MeOH) Lambda max: 261.4 nm
$^1$H-NMR δ(ppm in DMSO-$d_6$):
11.36 (s, 1H, $N_3'$—H)
7.88 (d, 1H, $C_6'$—H, J=8.1 Hz)
6.18 (t, 1H, $C_5$—H, J=4.8 Hz)
5.62 (d, 1H, $C_5'$—H, J=8.1 Hz)
5.33 (t, 1H, $C_2$—H, J=5.7 Hz)
5.17 (t, 1H, —OH, $D_2O$ exchange)
3.72 (t, 2H, $C_2$—$CH_2OH$, J=4.6 Hz)
3.41 (dd, 1H, $C_4$—H, J=5.7 and 12 Hz)
3.20 (dd, 1H, $C_4$—H, J=4.6 and 9.9 Hz)

Example 15

Cis- and trans-2-benzoyloxymethyl-5-(thymin-N-1'-yl)-1,3-oxathiolane

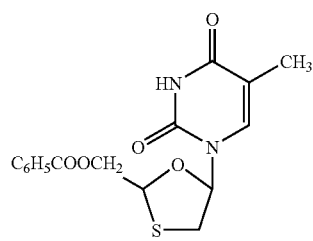

(LV)

1.7 g of thymine was heated at reflux in 50 ml of HMDS containing 50 mg of $(NH_4)_2SO_4$ until the solution became clear. The mixture was evaporated under reduced pressure. The residue was dried under high vacuum for 1 hour and dissolved in 150 ml of 1,2-dichloroethane.

3 g of 2-benzoyloxymethyl-5-ethoxy-1,3-oxathiolane was dried by evaporation twice with 75 ml of benzene and dissolved in 150 ml of dry 1,2-dichloroethane.

The silylated thymine solution was transferred into the oxathiolane through a canula under argon atmosphere. 3.3 ml of TMS-Triflate (trimethylsilyl-triflate) in 30 ml of dry 1,2-dichloroethane was introduced into the reaction mixture through a canula under argon atmosphere. The solution was heated at reflux under argon atmosphere for 36 hours, cooled to room temperature and poured into 300 ml of saturated aqueous $NaHCO_3$ solution. The organic layer was collected and the aqueous phase was extracted twice with methylene chloride (2×100 ml). The combined organic phase was washed twice with water (2×200 ml), once with NaCl solution (1×150 ml) and dried over $MgSO_4$. The solution was filtered. The filtrate was evaporated in vacuum. The residue was purified on silica gel using Hexane:EtOAc 1:1 as eluant. It yielded 1.3 g (35%) of pure product.

The product was shown as only one spot on TLC but the $^1$H-NMR spectrum indicated the presence of the two isomers cis and trans in a ratio of 1:1.2.

$R_f$: 0.30 in Hexane:EtOAc 2:3
U.V.: (MeOH) Lambda max: 266 nm
$^1$H-NMR δ(ppm in $CDCl_3$):
8.60 (broad singlett, $N_3'$—H)
8.06 (m, 2H, aromatic)
7.59 (m, 1H, aromatic)
7.49 (m, 2H, aromatic)
7.38 (d, 1H, $C_6'$—H-cis, J=1.3 Hz)
7.28 (d, 1H, $C_6'$—H-trans, J=1.3 Hz)
6.55 (dd, 1H, $C_5$—H-trans isomer, J=3.1 and 5.6 Hz)
6.38 (t, 1H, $C_5$—H-cis isomer, J=5.5 Hz)
5.78 (dd, 1H, $C_2$—H-trans, J=4.4 and 6.4 Hz)
5.46 (t, 1H, $C_2$—H-cis-isomer, J=4.3 Hz)
4.69 (d, 2H, $C_2$—$CH_2OCOC_6H_5$, J=4.2 Hz)
4.45 (m, 2H, $C_2$—$CH_2OCOC_6H_5$)
3.58 (m, 1H, $C_4$—H)
3.13 (m, 1H, $C_4$—H)
1.93 (d, 1H, $C_5'$—$CH_3$-trans isomer, J=1.2 Hz)
1.78 (d, 1H, $C_5'$—$CH_2$-cis isomers, J=1.2 Hz)

Example 16

Cis-2-hydroxymethyl-5-(thymin-N-1'-yl)-1,3-oxathiolane

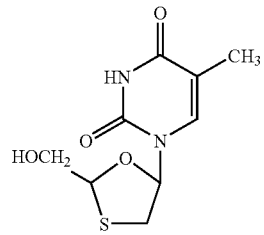

(LVI)

500 mg of a mixture cis- and trans-2-benzoyloxymethyl-5-(thymin-N-1'-yl)-1,3-oxathiolanes (XLIX) was dissolved in 100 ml of saturated methanolic ammonia. The mixture was stirred at room temperature overnight (18 hours). The mixture was then evaporated to dryness under reduced pressure. The residue was separated on silica gel using EtOAc:MeOH 98:2 as eluant.

The less polar product was identified as cis-isomer mp: 167–168° C.; $R_f$: 0.66 in EtOAc:MeOH 95:5 U.V.: (MeOH) Lambda max: 266 nm
$^1$H-NMR δ(ppm in DMSO-$d_6$)
11.38 (s, 1H, $N_3'$—H)
7.73 (d, 1H, $C_6'$—H, J=1.1 Hz)

6.16 (t, 1H, $C_5$—H, J=5.5 Hz)
5.31 (t, 1H, $C_2$—H, J=5.9 Hz)
5.14 (t, 1H, OH, $D_2O$ exchange)
3.70 (t, 2H, $C_2$—$CH_2OH$, J=5.1 Hz)
3.36 (dd, 1H, $C_4$—H, J=5.7 and 1.7 Hz)
3.16 (dd, 1H, $C_4$—H, J=5.5 and 11.7 Hz)
1.75 (d, 3H, $C_5'$—$CH_3$, J=1.7 Hz)

Example 17

Cis- and trans-2-benzoyloxymethyl-5-($N_4'$-acetyl-5'-fluoro-cytosin-1'-yl)-1,3-oxathiolane

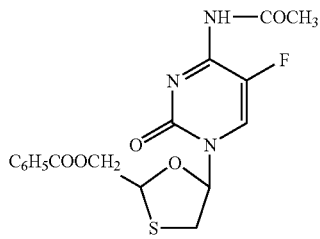

(LVII)

5-Fluorocytosine (4.30 g, 33.3 mmol), hexamethyldisilazane (25 ml) and ammonium sulfate (120 mg) were boiled under reflux until the cytosine dissolved (3 hours) and then further refluxed for 2 hours. The hexamethyldisilazane is evaporated in vacuo and toluene (100 ml) was added to the residue to co-evaporate the solvents. The resulting solution, bis(trimethylsilyl)-fluoro-cytosine in dichloromethane (40 ml) was added under argon to a solution of 2-benzoyloxymethyl-5-acetoxy-1,3-oxathiolane (8.537 g, 30.3 mmol) in dry dichloromethane (100 ml) and molecular sieves (4 Å, 2 g) previously prepared under argon and cooled at 0° C. for 20 minutes. [(Trifluoromethane-sulfonyl)oxy]trimethyl silane (6 ml, 31 mmol) was added to this mixture at 0° C. and the resulting solution was stirred at 25° C. for approximately 18 hours. The reaction mixture was then treated with 300 ml of saturated solution of sodium bicarbonate and stirred at room temperature for 2 hours. The filtrate was shaken two times with 300 ml of brine and one time with distilled water. The organic layer was dried over magnesium sulfate, filtered and evaporated to dryness. This afforded a crude 5-fluorocytosine derivative (10.1 g). $R_f$: 0.57 (EtOAc:MeOH 9:1)

This residue was acetylated in the next step without further purification. The crude material was dissolved in dry dichloromethane (120 ml) in a 500 ml round bottom flask under argon. Triethylamine (12.7 ml, 91.1 mmol) and dimethyl aminopyridine (111 mg, 0.9 mmol) were added to the solution. The flask was then immersed in an ice bath for 1 hour under argon. Acetic anhydride (4.3 ml, 45 mmol), distilled over sodium acetate, was syringed into the cooled flask. The mixture was stirred overnight and then carefully decanted into an erlenmeyer flask containing saturated sodium bicarbonate solution. The product was then washed with distilled water followed by brine solution. The methylene chloride portions were dried and evaporated under high vacuum to dryness, yielding an acetylated α/β mixture as a colorless foam, weighing 9.6 g after drying. Flash chromatography of this material using ethylacetate:methanol (9:1) afforded 3.1 g, 7.8 mmol (46%) pure trans-(LI) and 3.5 g, 8.9 mmol (30%) pure cis-(LI).

trans-isomer: $R_f$: 0.65 in ethyl acetate:methanol 9:1
U.V.: (MeOH) Lambda max: 309 nm
$^1$H-NMR δ (ppm in $CDCl_3$)
8.77 (b, 1H; $C_4'$—NH—Ac)
8.06 (m, 2H; aromatic)
7.70 (d, 1H; $C_6'$—H, $J_{6,F}$=6.3 Hz)
7.62 (m, 1H; aromatic)
7.49 (m, 2H; aromatic)
6.51 (dd, 1H; $C_5$—H)
5.91 (dd, 1H; $C_2$—H)
4.48 (dd, 2H; $C_2$—$CH_2OCOC_6H_5$)
3.66 (dd, 1H; $C_4$—H)
3.34 (dd, 1H; $C_4$—H)
2.56 (s, 3H; NH—$COCH_3$)
cis-isomer: $R_f$: 0.58 in ethyl acetate:methanol 9:1
U.V.: (MeOH) Lambda max: 309 nm
$^1$H-NMR δ (ppm in $CDCl_3$)
8.72 (b, 1H; $C_4'$—NH—Ac)
8.06 (m, 2H; aromatic)
7.87 (d, 1H; $C_6'$—H, $J_{6,F}$=6.2 Hz)
7.60 (m, 1H; aromatic)
7.49 (m, 2H; aromatic)
6.32 (dd, 1H; $C_5$—H)
5.47 (dd, 1H; $C_2$—H)
4.73 (dd, 2H; $C_2$—$CH_2OCOC_6H_5$)
3.62 (dd, 1H; $C_4$—H)
3.19 (dd, 1H; $C_4$—H)
2.55 (s, 3H; NH $COCH_3$)

Example 18

Cis- and trans-hydroxymethyl-5-(5'-fluorocytosin-1'-yl)-1,3-oxathiolane

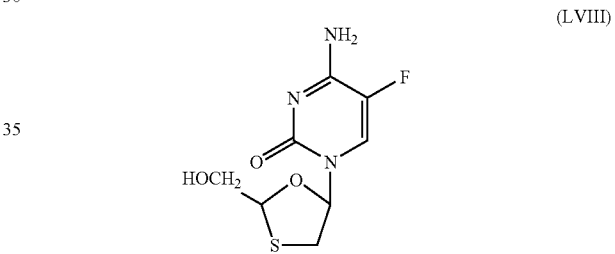

(LVIII)

1.0 g (2.54 mmol) of trans-2-benzoyloxymethyl-5-($N_4'$-acetyl-5'-fluoro-cytosin-1'-yl)-1,3-oxathiolane was stirred in 25 ml of methanolic ammonia at 0° C. for 1 hour and then overnight at room temperature. The mixture was evaporated under reduced pressure. The residue was triturated twice (2×30 ml) with anhydrous ether. The solid residue was recrystallized in absolute ethanol to give 484 mg (1.95 mmol, 77%) of desired product trans-(LII): m.p. 219–221° C.; $R_f$=0.21 in ethyl acetate: methanol (9:1), which was identified by $^1$H, $^{13}$C-NMR and U.V. Lambda max ($H_2O$) 280.9 nm.

1.2 (3.05 mmol) of cis-2-benzoyloxymethyl-5-($N_4'$-acetyl-5'-fluoro-cytosin-1'-yl)-1,3-oxathiolane was stirred in 30 ml of methanolic ammonia at 0° C. for 1 hour and then overnight at room temperature. The mixture was evaporated under reduced pressure. The residue was triturated twice (2×30 ml) with anhydrous ether. The solid residue was recrystallized in absolute ethanol to give 655 mg (2.64 mmol, 87%) of pure product cis-(LII): m.p. 204–206° C.; $R_f$=0.21 in ethylacetate: methanol (9:1). The desired compound was identified by $^1$H, $^{13}$C-NMR and U.V. Lambda max ($H_2O$) 280.9 nm.

trans-isomer:
$^1$H-NMR δ (ppm in DMSO-$d_6$):
7.85 (d, 1H; $C_6'$—H, $J_{CF}$=7.01 Hz)
7.83 (d, 2H; $C_4'$—$NH_2$)

6.30 (dd, 1H; $C_5$—$\underline{H}$)
5.60 (t, 1H; $C_2$—$\underline{H}$)
5.18 (t, 1H; $C_2$—$CH_2$—O$\underline{H}$)
3.49 (m, 3H; $C_2$—$C\underline{H}_2$OH+$C_4\underline{H}$)
3.17 (dd, 1H; $C_4$—$\underline{H}$)
$^{13}C$ NMR (DMSO-$d_6$), Varian XL 300); δ in ppm

| $C_2'$ | $C_4'$ | $C_5'$ | $C_6'$ |
|---|---|---|---|
| 153.47 | 158.20 ($^2J_{CF}$ = 13.2 Hz) | 134.65 ($J_{CF}$ = 26.2 Hz) | 126.24 ($^2J_{CF}$ = 32.0 Hz) |
| $C_5$ | $C_4$ | $C_2$ | $CH_2OH$ |
| 88.20 | 6.18 | 87.16 | 64.71 | cis-isomer:
$^1$H-NMR δ(ppm in DMSO-$d_6$)
8.22 (d, 1H; $C_6'$—H, $J_{CF}$=7.26 HZ)
7.84 (d, 2H; $C_4'$—N$\underline{H}_2$)
6.16 (t, 1H; $C_5$—$\underline{H}$)
5.43 (t, 1H; $C_2$—$CH_2$—O$\underline{H}$)
5.19 (t, 1H; $C_2$—$\underline{H}$)
3.77 (m, 2H; $C_2$—$C\underline{H}_2$OH)
3.35 (dd, 1H; $C_4$—$\underline{H}$)
3.12 (dd, 1H; $C_4$—$\underline{H}$)

| $C_2'$ | $C_4'$ | $C_5'$ | $C_6'$ |
|---|---|---|---|
| 153.46 | 158.14 ($^2J_{CF}$ = 14.0 Hz) | 134.63 ($J_{CF}$ = 24.1 Hz) | 126.32 ($J_{CF}$ = 32.5 Hz) |
| $C_5$ | $C_4$ | $C_2$ | $CH_2OH$ |
| 86.82 | 36.80 | 86.77 | 62.32 |

Example 19

2-chloromethyl-1,3-dioxolane-4-carboxylic acid

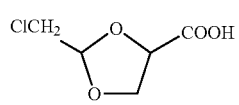

(XXVI)

Starting material (XXV) (40 g; prepared according to E. G. Hallonquist and H. Hibbert, Can. Res. J. 1933, 7, 129) was treated with pyridinium dichromate (PDC; 345 g) in dimethyl formamide (DMF; 690 ml) at 0° according to the procedure of E. J. Corey and G. Schmidt, Tetrahedron Lett., 1979, 399 and product (XXVI) obtained as a crude mixture of cis- and trans-isomers (20 g) was identified by its $^1$H NMR spectrum [200 MHz, CDCl$_3$; tetramethyl silane (TMS) as internal reference]. δ(ppm):

3.6–3.8 (m, 2H; $C\underline{H}_2$Cl);
4.1–4.5 (m, 2H; $C_5\underline{H}_2$);
4.72–4.797 (qq, 1H; $C_4$—$\underline{H}$);
5.29–5.46 (tt, 1H; $C_2$—$\underline{H}$).

The product was used as such in the next step.

Example 20

Cis- and trans-2-chloromethyl-4-m-chlorobenzoyloxy-1,3-dioxolane

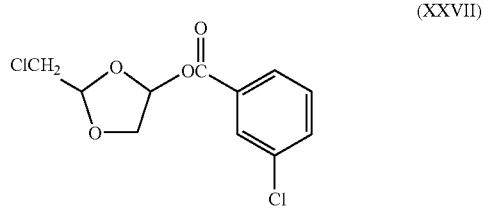

(XXVII)

The preceding product (XXVI) (5.26 g) was treated in CH$_2$Cl$_2$ at –20' with 3.6 ml of ethyl chloro-formate in the presence of 4.5 of triethylamine. To the solution was added 8.85 g of m-chloroperbenzoic acid at room temperature according to the procedure of D. H. R. Barton, I. H. Coates and P. G. Sammes, J. Chem. Soc., Perkin 1, 1973, 599 to give (XXVII) as a mixture of cis- and trans-isomers. These were separated and purified by flash chromatography on silica gel using a mixture of hexanes and ethyl acetate as the eluent. The isomers were identified by their $^1$H NMR spectra (recorded as in example 19):

trans-isomer of (XXVII): δ(ppm):
3.66 (q, 2H; $C\underline{H}_2$—Cl);
4.36 (qq, 2H; $C_5$—$\underline{H}_2$);
5.57 (t, 1H; $C_2$—$\underline{H}$);
6.7 (q, 1H; $C_4$—$\underline{H}$);
7.39–8.0 (m, 4H; aromatic $\underline{H}$);
cis-isomer of (XXVII): δ(ppm):
3.66 (q, 2H; $C\underline{H}_2$Cl);
4.24 (qq, 2H; $C_5$—$\underline{H}_2$);
5.43 (t, 1H; $C_2$—$\underline{H}$);
6.63 (q, 1H; $C_4$—$\underline{H}$);
7.42–8.04 (m, 4H; aromatic $\underline{H}$).

Example 21

2-chloromethyl-4-(thymin-1'-yl)-1,3-dioxolane

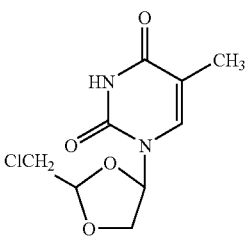

(XXVIII)

Reaction of the preceding compound with thymine was carried out according to the procedure of D. S. Wise and L.

B. Townsend, in Nucleic Acid Chemistry, Eds. L. B. Townsend and R. S. Tipson, John Wiley & Sons, Inc., New York, 1978, Part 1, pp. 413–419. The product was a mixture of cis- and trans-isomers of (XXVIII) (37.3 mg from 131 mg of (XXVII)) which had the following $^1$H NMR characteristics (obtained as in example 19): δ(ppm):

1.93 (d, 3H; 5'—C$\underline{H}_3$);
3.64 and 3.85 (dd, 2H; C$\underline{H}_2$Cl);
4.17–4.46 (m, 2H; C$_5$—$\underline{H}_2$);
5.26 and 5.72 (tt, 1H; C$_2$—$\underline{H}$);
6.6 and 6.66 (qq, 1H; C$_4$—$\underline{H}$);
7.40 and 7.49 (dd, 1H; C$_6$—$\underline{H}$);
U.V.: (CH$_3$OH) max. 264 nm.

Example 22

Cis- and trans-2-acetoxymethyl-4-(thymin-1'-yl)-1, 3-dioxolane

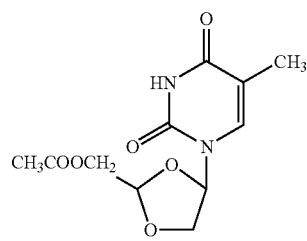
(XXIX)

The preceding compound (XXVIII) (35 mg) was reacted with anhydrous potassium acetate (70 mg) in boiling DMF (3 ml) for 4 h to give after conventional workup a cis- and trans-mixture of (XXIX) (25 mg). These isomers were purified and separated by flash chromatography on silica using a mixture of hexanes and ethyl acetate as the eluent. Their $^1$H NMR spectra were as follows:

trans-isomer of (XXIX): δ(ppm):
1.94 (d, 3H; C$_5$'—C$\underline{H}_3$);
2.12 (s, 3H; C$\underline{H}_3$CO$_2$—);
4.05–4.43 (m, 4H; C$_2$—C$\underline{H}_2$—O$_2$CCH$_3$ and C$_5$—$\underline{H}_2$);
5.65 (t, 1H; C$_2$—$\underline{H}$);
6.31 (q, 1H; C$_4$—$\underline{H}$);
7.14 (d, 1H; C$_{6'}$—$\underline{H}$);
8.18 (m, 1H; N$_3$—$\underline{H}$).

cis-isomer of (XXIX): δ(ppm):
1.97 (d, 3H; C$_5$'C$\underline{H}_3$);
2.14 (s, 3H; C$\underline{H}_3$CO—O);
4.13–4.49 (m, 4H; 2-C$\underline{H}_2$OCOCH$_3$ and C$_5\underline{H}_2$);
5.19 (t, 1H; C$_2$—$\underline{H}$);
6.40 (q, 1H; C$_4\underline{H}$);
7.43 (d, 1H; C$_{6'}$—$\underline{H}$);
8.12 (m, 1H; N$_3$,—$\underline{H}$).
U.V.: (CH$_3$OH) max. 264 nm.

Example 23

Cis- and trans-2-hydroxymethyl-4-(thymin-1'-yl)-1, 3-dioxolane

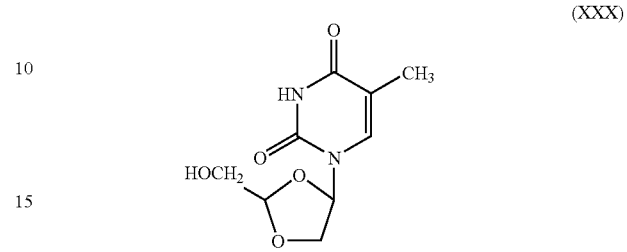
(XXX)

The preceding trans- and cis-isomers of XXIX (10 mg) were respectively treated with a catalytic amount of potassium carbonate in methanol (5 ml) at room temperature for 5–6 h and the mixture worked up in the usual manner and the respective products purified by flash chromatography on silica gel using a mixture of ethyl acetate and methanol as the eluent. The $^1$H NMR spectrum of the pure trans-isomer of (XXX) was as follows (in CD$_3$COCD$_3$ as solvent);

trans-(XXX): δ(ppm):
1.87 (d, 3H; C$_5$'—C$\underline{H}_3$);
3.61 (q; 2H; C$_2$—C$\underline{H}_2$OH);
4.30 (qq, 2H; C$_5$—$\underline{H}_2$);
5.56 (t, 1H; C$_2$—$\underline{H}$);
6.31 (q, 1H; C$_4$—$\underline{H}$);
7.41 (d, 1H; C$_{6'\underline{H}}$.
U.V.: (CH$_3$OH) max. 265 nm.

cis-isomer of (XXX) (in CD$_3$COCD$_3$): δ(ppm):
1.82 (d, 3H; C$_5$'—C$\underline{H}_3$);
3.82 (q, 2H; C$_2$C$\underline{H}_2$OH);
4.24 (qq, 2H; C$_5$—$\underline{H}_2$);
5.02 (t, 1H; C$_2$—$\underline{H}$);
6.34 (q, 1H; C$_4$—$\underline{H}$);
7.81 (d, 1H; C$_{6'}$—$\underline{H}$).
U.V.: (CH$_3$OH) max. 264 nm.

Example 24

2-benzoyloxymethyl-4-hydroxymethyl-1,3-dioxolane

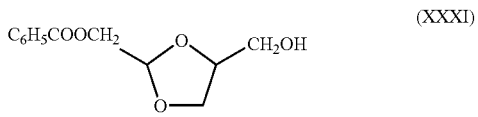
(XXXI)

Starting material XXV (41.6) was treated with potassium benzoate (65.56 g) in boiling dimethyl formamide containing 100 mg of 18-crown-6 for 24 h after which time the mixture was worked up in the usual manner and the product (51.02 g) characterized by its $^1$H NMR spectrum (CDCl$_3$; TMS): δ(ppm):
3.5–4.8 (m7H; C$_5$—$\underline{H}_2$; C$_2$—C$\underline{H}_2$OCOC$_6$H$_5$,C$_4$—C$\underline{H}_2$OH and C$_2$—$\underline{H}$);
5.05 and 5.16 (tt, 1H; C$_4$—$\underline{H}$);
7.27–8.10 (m, 5H; aromatic $\underline{H}$).

Similar results were obtained using potassium acetate instead of potassium benzoate.

Example 25

2-benzoyloxymethyl-1,3-dioxolane-4-carboxylic acid

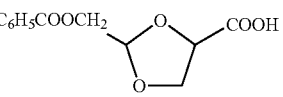
(XXXII)

The preceding compound (XXXI) (51.02 g) was treated at 0° with pyridinium dichromate (282.5 g) in dimethyl formamide (565 ml) and the mixture worked up in the usual manner to give 35 g of crude (XXXII) which was used as such in the next example.

Example 26

Cis- and trans-2-benzoyloxymethyl-4-(m-chlorobenzoyloxy)-1,3-dioxolane

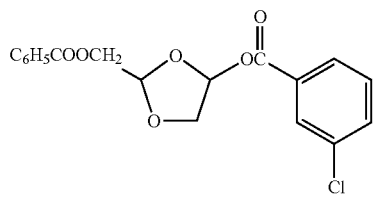
(XXXIII)

A 10 g portion of crude (XXXII) was treated with 6.03 ml of ethyl chloroformate in the presence of 8.6 ml of triethylamine followed by the addition of 16.81 g of m.chloroperbenzoic acid exactly as described in example 20 for the case of the preparation of intermediate (XXVII). The isomers of product (XXXIII) thus obtained were purified by flash chromatogaphy on silica gel using a mixture of hexanes and ethyl acetate as the eluent. They were characterized by their $^1$H NMR spectra (CDCl$_3$);

trans-isomer of (XXXIII): δ(ppm):
  4.29 (qq, 2H; $C_5$—$H_2$);
  4.49 (d, 2H; $C_2$—$CH_2OCOC_6H_5$);
  5.66 (t, 1H; $C_2$—$H$);
  6.70 (q, 1H; $C_4$—$H$);
  7.27–8.10 (m, 9H; aromatic)

cis-isomer of (XXXIII): δ(ppm):
  4.27 (qq, 2H; $C_5$—$H_2$);
  4.51 (d, 2H; $C_2$—$CHOCOC_6H_5$);
  5.51 (t, 1H; $C_2$—$H$);
  6.59 (d, 1H; $C_4$—$H$);
  7.26–8.09 (m, 9H; aromatic).

Example 27

2-benzoyloxymethyl-4-(cytosin-1'-yl)-1,3-dioxolane

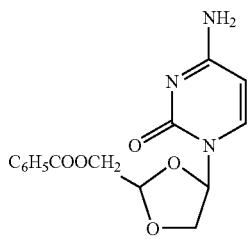
(XXXIV)

Following the procedure described by T. Ueda and S. I. Watanabe, Chem. Pharm. Bull. (Japan), 1985, 33, 3689–3695 and by G. Gosselin, M. C. Bergogne, J. DeRudder, E. DeClercq and J. L. Imbach, J. Med., Chem, 1987, 30, 982–991, cytosine (139 mg) and either isomer of the preceding compound (XXXIII) (363 mg) yielded a mixture of cis- and trans-isomers (390 mg) (XXXIV) which were used as such in the following step.

Example 28

Cis- and trans-2-benzoyloxymethyl-4-(N-acetylcytosin-1'-yl)-1,3-dioxolane

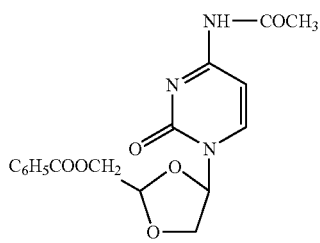
(XXXV)

Treatment of cis- and trans-(XXXIV) with excess acetic anhydride in pyridine at room temperature yielded after work up in the conventional manner, a mixture of the cis- and trans-isomers of (XXXV) which were separated and purified by flash chromatography on silica gel using a mixture of hexanes and ethyl acetate as the eluent. They were characterized by their $^1$H NMR spectra (CDCl$_3$):

trans-isomer of (XXXV): δ(ppm):
  2.15 (s, 3H; $C_4$—NH—$COCH_3$);
  4.16 and 4.46 (m, 4H; $C_5$—$H_2$ and $C_2$—$CH_2OCOC_6$—$H_5$);
  5.96 (t, 1H; $C_2$—$H$);
  6.24 (q, 1H; $C_4$—$H$);
  7.55–8.09 (m, 5H; aromatic);
  8.15 (d, 1H; $C_{6'}$—$H$)

cis-isomer of (XXXV): δ(ppm):
  2.15 (s, 3H; $C_{4'}$—NH—$COCH_3$);
  4.26 and 4.56 (m, 4H; $C_5$—$H_2$ and $C_2$—$CH_2OCOC_6$—$H_5$);
  5.35 (t, 1H; $C_4$—$H$);
  6.25 (q, 1H; $C_4$—$H$);
  7.18 (d, 1H; $C_{5'}$—$H$);
  7.58–8.04 (m, 5H; aromatic)
  8.17 (d, 1H; $C_{6'}$—$H$).

Example 29

Cis- and trans-2-hydroxymethyl-4-(cytosin-1'-yl)-1,3-dioxolane

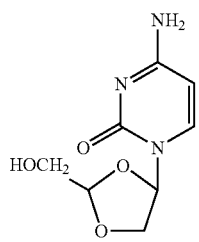

(XXXVI)

Each of the preceding isomers of (XXXV) (25 mg) was treated with potassium carbonate (20 mg) in methanol at room temperature for several hours and the mixtures worked in the usual manner to yield each isomer of (XXIV) which were purified by chromatography on silica gel using a mixture of ethyl acetate and methanol an eluent. They were crystallized from methanol and characterized by their respective $^1$H NMR spectra (CD$_3$COCD$_3$):

trans-isomer of (XXXVI): m.p. 179.180° δ(ppm):
3.62 (q, 2H; $C_2$—$CH_2OH$);
4.21 (qq, 2H; $C_5$—$H_2$);
5.50 (t, 1H; $C_2$—$H$);
5.93 (d, 1H; $C_5$,—$H$, J=7.5 Hz);
6.18 (q, 1H; $C_4$—$H$);
7.66 (d, 1H; $C_6$,—$H$, J=7.5 Hz).
U.V.: (CH$_3$OH) max. 271 nm.
cis-isomer of (XXXVI): m.p. 173–174° δ(ppm):
3.82 and 4.15 (m, 4H; $C_5$—$H_2$ and $C_2$—$CH_2OH$);
5.04 (t, 1H; $C_2$—$H$);
5.83 (d, 1H; $C_5$—$H$);
6.23 (q, 1H; $C_4$—$H$);
8.05 (d, 1H; $C_6$,$H$);
U.V.: (CH$_3$OH) max. 270 nm.

Example 30

Cis- and trans-2-benzoyloxymethyl-4-(adenin-9'-yl)-1,3-dioxolane

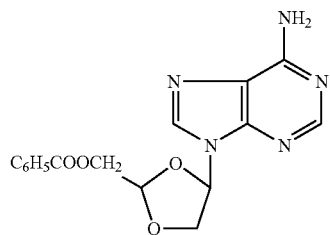

(XXXVII)

Following the same procedure as in example 27, adenine (135 mg) was coupled with either isomer of intermediate XXXIII (545 mg) in dimethylformamide at 1200 in the presence of trimethylsilyl triflate (0.45 ml) and the mixture worked up in the usual manner to yield a mixture of cis- and trans-isomers of (XXXVII) (540 mg) which were purified and separated by chromatography on silica gel using a mixture of hexanes and ethyl and acetate as the eluent. They were characterized by their respective $^1$H NMR spectra (CDCl$_3$):

trans-isomer of (XXXVII): δ(ppm):
4.5 and 4.59 (m, 4H; $C_5$—$H_2$ and $C_2$—$CH_2OCOC_6H_5$);
6.00 (t, 1H; $C_2$—$H$);
6.65 (q, 1H; $C_4$—$H$);
6.75 (m, 2H; $C_6H_2$);
7.68–8.21 (m, 5H; aromatic);
8.36 (s, 1H; $C_2$,—$H$);
8.37 (s, 1H; $C_8$,—$H$).
cis-isomer of (XXXVII): δ(ppm):
4.62 (d, 2H; $C_2$—$CH_2OCOC_6H_5$);
4.65 (qq, 2H; $C_5$—$H_2$);
5.52 (t, 1H; $C_2$—$H$);
6.59 (q, 1H; $C_4$—$H$);
6.85 (m, 2H; $C_6$,—$NH_2$);
6.96–7.71 (m, 5H; aromatic);
7.66 (d, 2H; $C_2$,—$H$ and $C_8$,—$H$).

Example 31

Cis- and trans-2-hydroxymethyl-4-(adenin-9'-yl)-1,3dioxolane

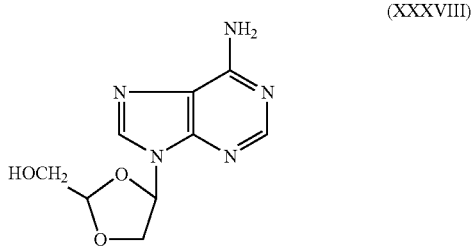

(XXXVIII)

Each isomer of the preceding compound (XXXVII) was treated with potassium carbonate in methanol at room temperature by the same procedure described in example 23 and each product purified by column chromatography on silica gel using a mixture of ethyl acetate and methanol as the eluent. The isomers were further purified by crystallization from methanol and characterized by their $^1$N NMR spectra (CD$_3$SOCD$_3$):

trans-isomer of (XXXVIII): δ(ppm):
3.50 (d, 2H; $C_2$—$CH_2OH$);
4.70 (m, 2H$C_5$—$H_2$);
5.52 (t, 1H; $C_2$—$H$);
6.44 (q, 1H; $C_4$—$H$);
8.18 (s, 1H; $C_2$,—$H$);
8.31 (s, 1H; $C_8$,—$H$).
U.V.: (CH$_3$OH) max. 269 nm.
cis-isomer of (XXXVIII): δ(ppm):
4.63 (d, 2H; $C_2$—$CH_2OH$);
4.29 (qq, 2H; $C_5$—$H_2$);
5.08 (t, 1H; $C_2$—$H$);
6.43 (q, 1H; $C_4$—$H$);
8.18 (s, 1H; $C_2$,—$H$);
8.36 (s, 1H; $C_8$,—$H$).
U.V.: (CH$_3$OH) max. 269 nm.

Example 32

Cis- and trans-2-benzoyloxymethyl-4-(2'-amino-6'-chloro-purin-9'-yl)-1,3-dioxolane

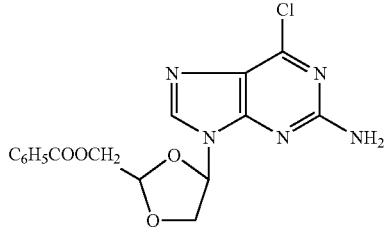

(XXXIX)

A solution of 2-amino-6-chloropurine (600 mg; 3.54 mmol) in 20 ml of hexamethyldisilazane (HMDS) containing 0.5 ml of trimethylsilyl chloride (TMS-Cl) was heated under reflux for 3 h after which time the mixture was evaporated to dryness in vacuo. The residue was dissolved in 75 ml of dichloroethane containing 910 mg of compound (XXXIII) and 0.6 ml of trimethylsilyl triflate (TMS-T$_f$) added. After refluxing under argon for 4 h, the mixture was collected, 2 g of solid NaHCO$_3$ added followed by 50 ml of saturated aqueous NaHCO$_3$. The organic layer was collected and after work-up in the usual manner, crude (XXVII) was obtained as an oil which was purified and separated into its isomer by chromatography on silica gel using hexane-ethyl acetate (3:7) as the eluent to give 230 mg of pure trans- and 250 mg or pure cis-isomer as colorless foams. They were characterized by their $_1$H NMR spectra (CDCl$_3$):

trans-isomer of (XXXIX)

R$_f$: 0.40; hexane-EtOAc 3:7 δ(ppm):
4.45–4.52 (m, 4H; C$_5$—$\underline{H}_2$,C$_2$—C$\underline{H}_2$OCOC$_6$H$_5$);
5.16 (b, 2H; C$_{2'}$—NH$_2$);
5.83 (t, 1H; C$_2$—$\underline{H}$, J=3.8 Hz);
6.39 (dd, 1H; C$_4$—$\underline{H}$);
7.41–7.58 (m, 3H; aromatic);
7.92 (s, 1H; C$_{8'}$—$\underline{H}$);
8.06 (d, 2H; aromatic, J=7 Hz).
U.V.: (CH$_3$OH) max. 312 nm.

cis-isomer of (XXXIX):
R$_f$: 0.26, hexane-EtOAc 3:7 δ(ppm):
4.25–4.33 (dd, 1H; C$_5$—H, J=5.43 Hz);
4.59–4.64 (m, 3H; C$_5$—H and C$_2$—CH$_2$—OCOC$_6$H$_5$);
5.17 (b, 2H; C$_{2'}$—NH$_2$);
5.42 (t, 1H; C$_2$—$\underline{H}$, J=3.50 Hz);
6.33–6.53 (dd, 1H; C$_4$—H);
7.38–7.57 (m, 3H; aromatic);
7.93–7.98 (d, 2H; aromatic);
8.00 (s, 1H; C$_{8'}$—H).
U.V.: (CH$_3$OH) max. 312 nm.

Example 33

Cis- and trans-2-hydroxymethyl-4-(2'-amino-6'-chloro-purin-9'-yl)-1,3-dioxolane

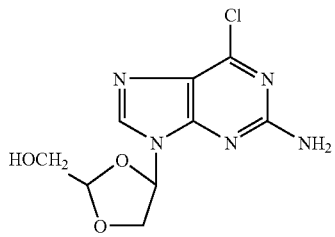

(XL)

The preceding trans-isomer of (XXXIX) (180 mg) was dissolved in 30 ml of methanol, the solution cooled to 0° and dry ammonia bubbled through for 15 min. After stirring at room temperature for 15 h, the solvent was removed in vacuo and the residue crystallized from ether. After recrystallization from ethanol-ether, 98 mg of pure trans-(XL), m.p. 155–156°, was obtained (R$_f$: 0.23, EtOAc). It was characterized by $^1$H NMR (DMSO-d$_6$):

trans-(XL): δ(ppm):
3.44–3.49 (m, 2H; C$_2$—C$\underline{H}_2$OH);
4.37–4.45 (m, 2H; C$_5$—$\underline{H}_2$);
5.01 (t, 1H; C$_5$—CH$_2$O$\underline{H}$, J=6.2 Hz);
5.46 (t, 1H; C$_2$—$\underline{H}$, J=3.6 Hz);
6.27–6.32 (dd, 1H; C$_4$—$\underline{H}$, J=4,1 Hz);
7.00 (b, 2H; C$_{2'}$—N$\underline{H}_2$);
8.26 (s, 1H; C$_{8'}$—$\underline{H}$).
U.V.: (CH$_3$OH) max. 247 and 308 nm.

The cis-isomer of (XL) was obtained in similar yield from the cis-isomer of (XXXIX) by the same preceding procedure. After recrystallization from ethanol-ether, the pure product had m.p. 145–147° (R$_f$: 0.24, EtOAc). It was characterized by $^1$H NMR (DMSO-d$_6$): cis-(XL): δ(ppm):
3.54–3.59 (m, 2H; C$_2$—C$\underline{H}_2$OH);
4.12–4.19 (dd, 1H; C$_5$—H, J=5.3 Hz and 9.8 Hz);
4.48–4.53 (d, 1H; C$_5$—H, J=9.8 Hz);
5.01 (t, 1H; C$_2$—$\underline{H}$, J=2.8 Hz);
5.09 (t, 1H; C$_2$—CH$_2$—O$\underline{H}$, J=6.0 Hz);
6.24 (d, 1H; C$_4$—H, J=5.1 Hz);
6.96 (b, 2H; C$_{2'}$—NH$_2$);
8.23 (s, 1H; C$_{8'}$—H).
U.V.: (CH$_3$OH) max. 247 and 308 nm.

Example 34

Cis- and trans-2-hydroxymethyl-4-2'-amino-purin-9'-yl)-1,3-dioxolane

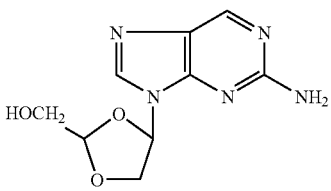

(XLI)

The preceding trans-isomer of (XL) (50 mg) was submitted to hydrogenation conditions under 50 psi of hydrogen over 10% Pd/C (30 mg) in 30 ml of ethanol containing 0.5 ml of triethylamine. After 3 h of shaking, the mixture was worked up in the usual manner to yield a solid which was recrystallized from ethanol-ether to give 36 mg of pure trans-(XLI), m.p. 153–155°, $R_f$: 0.25 (EtOAc: MeOH 85:15). It was characterized by $^1$H NMR (DMSO-$d_6$): trans-(XLI): δ(ppm):

3.44–3.49 (m, 2H; $C_2$—$CH_2$OH);
4.38–4.44 (m, 2H; $C_5$—$H_2$);
4.99 (t, 1H; $C_2$—$CH_2$—$OH$, J=6.1 Hz);
5.45 (t, 1H; $C_2$—$H$, J=3.6 Hz);
6.29–6.34 (dd, 1H; $C_4$—$H$);
6.59 (b, 2H; $C_{2'}$—$NH_2$);
8.19 (s, 1H; $C_{8'}$—$H$);
8.59 (s, 1H; $C_{6'}$—$H$).

The cis-isomer of (XLI) was obtained in similar yield from the cis-isomer of (XL) by the same preceding procedure. After recrystallization from ethanol-ether, the pure product had m.p. 145–148°, $R_f$: 0.25 (EtOAc:MeOH 85:15). It was characterized by $^1$H NMR (DMSO-$d_6$):

cis-(XLI): δ(ppm):
3.55–3.60 (dd, 2H; $C_2$—$CH_2$H, J=2.10 and 6.1 Hz);
4.14–4.22 (dd, 1H; $C_5$—$H$, J=5.4 and 9.7 Hz);
4.47–4.53 (dd, 1H; $C_5$—$H$, J=1.38 and 9.7 Hz);
5.02 (t, 1H; $C_2$—$H$, J=3 Hz);
5.11 (t, 1H; $C_2$—$CH_2OH$, J=7.2 Hz);
6.58 (b, 2H; $C_{2'}$—$NH_2$);
8.19 (s, 1H; $C_{8'}$—$H$);
8.57 (s, 1H; $C_{6'}$—$H$).
U.V.: ($CH_3OH$) max. 255, 308 nm.

Example 35

Cis- and trans-2-hydroxymethyl-4-(2',6'-diamino-purin-9'-yl)-1,3-dioxolane

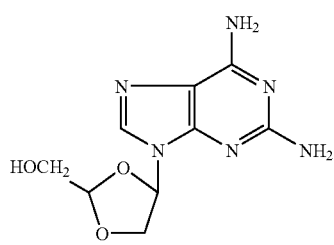

(XLII)

The above compound trans-(XXXIX) (200 mg) was dissolved in 30 ml of methanol saturated at 0° with dry ammonia and the solution heated in a steel bomb to 105–110° for 16 h. The solution was evaporated to dryness and the residue purified by chromatography on silica gel using chloroform-methanol 4:1 as the eluent to give 101 mg of product which was recrystallized from methanol-ether to yield pure trans-(XLII), m.p. 165–168°, $R_f$: 0.30 ($CHCl_3$; $CH_3OH$ 4:1). It was characterized by $^1$H NMR (DMSO-$d_6$): trans-(XLII): δ(ppm):

3.43–3.48 (m, 2H; $C_2$—$CH_2$OH);
4.34–4.49 (m, 2H; $C_5$—$H_2$);
4.97 (t, 1H; $C_2$—$CH_2OH$);
5.42 (t, 1H; $C_2$—$H$);
5.82 (b, 2H; $C_{2'}$— or $C_{6'}$—$NH_2$);
6.18–6.23 (dd, 1H; $C_4$—$H$);
6.72 (b, 2H; $C_{2'}$— or $C_{6'}$—$NH_2$);
7.84 (s, 1H; $C_{8'}$—$H$).
U.V.: ($CH_3OH$) max. 255,280 nm.

The cis-isomer of (XLII) was obtained by the same preceding procedure from compound cis-(XXXIX). After recrystallization from methanol-ether, pure cis-(XLII), m.p. 180–182°, $R_f$: 0.32 ($CHCl_3$—$CH_3OH$ 4:1) was obtained in a similar yield. It was characterized by $^1$H NMR (DMSO-$d_6$): cis-(XLII): δ(ppm):

3.56–3.58 (d, 2H; $C_2$—$CH_2$OH, J=4.2 Hz);
4.11–4.19 (dd, 1H; $C_5$—$H$, J=4.5 and 9.7 Hz);
4.38–4.44 (dd, 1H; $C_5$—$H$, J=1.6 and 11.2 Hz);
5.00 (t, 1H; $C_2$—$H$, J=3.1 Hz);
5.91 (b, 2H; $C_{2'}$— or $C_{6'}$—$NH_2$);
6.15–6.19 (dd, 1H; $C_4$—$H$);
6.84 (b, 2H; $C_{2'}$— or $C_{6'}$—$NH_2$);
7.86 (s, 1H; $C_{8'}$—$H$).
U.V.: ($CH_3OH$) max. 254,279 nm.

Example 36

Cis- and trans-2-hydroxymethyl-4-(guanin-9'-yl)-1,3-dioxolane

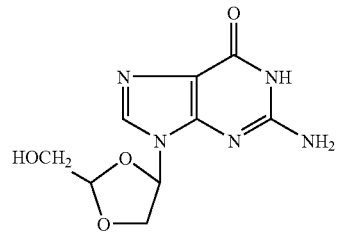

(XLIII)

The above cis-(XL) (40 mg) was dissolved in a mixture of 15 ml of methanol, 2 ml of water and 2 g of sodium hydroxide and the solution heated under reflux for 5 h after which time it was diluted with 100 ml of water and excess pyridinium sulfonate resin added. The slurry was filtered, the resin washed with water and the combined aqueous filtrates evaporated to dryness in vacuo to leave a residue which was taken up in 50% aqueous methanol. The solution was treated with activated charcoal, filtered and the filtrate evaporated to dryness in vacuo to give a solid residue that was recrystallized from ethanol-water to yield pure cis-XLIII (27 mg) m.p. >250° decomp., $R_f$:0.23 ($CHCl_3$: $CH_3OH$ 7:3). It was characterized by $^1$H NMR (DMSO-$d_6$): cis-(XLIII): δ(ppm):

3.55 (m, 2H; $C_2CH_2OH$);
4.10–4.17 (dd, 1H; $C_5$—$H$, J=5.6 and 9.8 Hz);
4.37–4.42 (dd, 1H; $C_5$—$H$, J=1.4 and 9.6 Hz);
4.98 (t, 1H; $C_2$—$H$, J=3.2 Hz);
5.15 (b, 1H; $C_2$—$CH_2OH$);
6.10–6.13 (dd, 1H; $C_4$—$H$, J=2.4 and 5.3 Hz);
6.66 (b, 2H; $C_{2'}$—$NH_2$);
7.78 (s, 1H; $C_{8'}$—$H$);
11.02 (b, 1H; $N_1$—$H$).
U.V.: ($CH_3OH$) max. 252, 270 (shoulder).

The isomer trans-(XLIII) was obtained in similar yield from the above trans-(XL) by the same preceding procedure. After recrystallization from ethanol-water, pure trans-(t), m.p. >260° (dec.), $R_f$:0.23 ($CHCl_3$:CH OH 7:3) was obtained and characterized by $^1$H NMR (DMSO-$d_6$): trans-(XLIII): δ(ppm):

3.42–3.47 (m, 2H; C$_2$—CH$_2$OH);
4.34 (d, 2H; C$_5$—H$_2$, J=4.8 Hz);
4.99 (t, 1H; C$_2$—CH$_2$OH);
5.40 (t, 1H; C$_2$—H, J=3.5 Hz);
6.15–6.20 (t, 1H; C$_4$—H, J=4.8 Hz);
6.49 (b, 2H; C$_{2'}$—NH$_2$);
7.83 (s, 1H; C$_{8'}$—H);
10.64 (b, 1H; N$_{1'}$—H).
U.V.: (CH$_3$OH) max. 252, 270 (shoulder)

Example 37

Tablet Formulations

A. The following formulation is prepared by wet granulation of the ingredients with a solution of povidone in water, drying and screening, followed by addition of magnesium stearate and compression.

|     |                        | mg/tablet |
|-----|------------------------|-----------|
| (a) | Active ingredient      | 250       |
| (b) | Lactose B.P.           | 210       |
| (c) | Povidone B.P.          | 15        |
| (d) | Sodium Starch Glycolate| 20        |
| (e) | Magnesium Stearate     | 5         |
|     |                        | 500       |

B. The following formulation is prepared by direct compression; the lactose is of the direct compression type.

|                    | mg/tablet |
|--------------------|-----------|
| Active ingredient  | 250       |
| Lactose            | 145       |
| Avicel             | 100       |
| Magnesium Stearate | 5         |
|                    | 500       |

C. (Controlled Release Formulation) The formulation is prepared by wet granulation of the ingredients (below) with a solution of povidone in water, drying and screening followed by the addition of magnesium stearate and compression.

|     |                                              | mg/tablet |
|-----|----------------------------------------------|-----------|
| (a) | Active ingredient                            | 500       |
| (b) | Hydroxypropylemethylcellulose (Methocel K4M Premium) | 112 |
| (c) | Lactose B.P.                                 | 53        |
| (d) | Povidone B.P.                                | 28        |
| (e) | Magnesium Stearate                           | 7         |
|     |                                              | 700       |

Example 38

Capsule Formulation

A capsule formulation is prepared by admixing the ingredients below and filling into a two-part hard gelatin capsule.

|                    | mg/capsule |
|--------------------|------------|
| Active ingredient  | 125        |
| Lactose            | 72.5       |
| Avicel             | 50         |
| Magnesium Stearate | 2.5        |
|                    | 250        |

Example 39

Injectable Formulation

Active ingredient 0.200 g

Sodium hydroxide solution, 0.1M q.s. to a pH of about 11.

Sterile water q.s. to 10 ml.

The active ingredient is suspended in some of the water (which may be warmed) and the pH adjusted to about 11 with a solution of sodium hydroxide. The batch is then made up to volume and filtered through a sterilizing grade membrane filter into a sterile 10 ml glass vial and sealed with sterile closures and overseas.

Example 40

Suppository

|                   | mg/suppository |
|-------------------|----------------|
| Active ingredient | 250            |
| Hard Fat, B.P.    | 1770           |
|                   | 2020           |

One-fifth of the hard fat is melted in a steam-jacketed pan at 45° C. maximum. The active ingredient is sifted through a 200 μm sieve and added to the molten base with mixing, using a high shear stirrer, until a smooth dispersion is achieved. Maintaining the mixture at 45° C., the remaining hard fat is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

Example 41

Antiviral Activity

All of the compounds of the preferred embodiments are novel and some are valuable for their properties as non-toxic inhibitors of the primary replication of HIV-1 in previously uninfected T-lymphocytes over a prolonged period of time.

In vitro testing was conducted on several of the compounds of this invention to determine their inhibitory properties. The results are shown in Tables 1, 2 and 3. The concentrations reported are μg/ml in the incubation media which affect the susceptibility of a continuous line of T-cells developed at the Lady Davis Institute for Medical Research (Montreal) by Dr. Mark A. Wainberg toward infection by HIV-1 following a protocol similar to that of H. Mitsuya and S. Broder, "Inhibition of the in vitro infectivity and cytopathic effect of human T-lymphotropic virus type III/lymphadenopathy-associated virus (HTLV-III/LAV) by 2',3'-dideoxynucleosides", *Proc. Natl. Acad. Sci. USA*, 83, pp. 1911–15 (1986). Protection of the cell line from infection was monitored by staining with monoclonal antibodies against viral proteins in the standard manner (Table 1). In all experiments, comparisons were made with the drug AZT as the control. In order to confirm the results, the drug effects were monitored by measuring reverse transcriptase (RT) activity in the U-937 line of human monocytic cells as assayed in the usual manner with tritiated thymidine triphosphate (TTP) (Table 2). The drug effects on cell viability as measured by the well-know cytolytic effects of HIV-1 on the MT-4 cell line was evaluated in the accepted manner (Table 1).

Toxicity

No toxic effects were observed in the above tests.

TABLE 1

Inhibition of HIV-1 product by compounds of formula (I) in MT-4 cells a) Viable cell counts (6 days in culture) using 2 μg/ml of compound

| Compound | Cell Viability % |
| --- | --- |
| no drug | 6.47 |
| AZT | 88.6 |
| cis-XI | 87.4 |
| trans-XI | 24 |
| cis-XII (b) | 14 |
| cis-LVI | 11 |
| cis-LIII | 18 |
| cis-XVIII | 14 | b) P-24 immunofluorescence

| Time in Culture | % Immunofluorescent Cells | | |
| --- | --- | --- | --- |
| (Days) | No Drug | 2 μg/ml AZT | 2 μg/ml cis-XI |
| 3 | 5.9 | 1.0 | 1.0 |
| 6 | 99 | 1.0 | 7.6 | c) Reverse transcriptase assay

| Time in Culture | RT Activity (CPM × 1000)/ml | | |
| --- | --- | --- | --- |
| (Days) | No Drug | 2 μg/ml AZT | 2 μg/ml cis-XI |
| 3 | 36.43 | 1.564 | 2.381 |
| 6 | 339.0 | 1.748 | 2.301 |

TABLE 2

Inhibition of HIV-1 production by compounds of formula (I) in H-9 cells
Reverse transcriptase assay

| Time in Culture | RT Activity (CPM × 1000)/ml | | |
| --- | --- | --- | --- |
| (Days) | No Drug | 2 μg/ml AZT | 2 μg/ml cis-XI |
| 5 | 9.117 | 3.346 | 3.077 |
| 8 | 438.5 | 3.414 | 5.853 |
| 11 | 2550 | 2.918 | 3.560 |
| 14 | 2002 | 8.320 | 2.872 |
| 7 | 584.5 | 2.997 | 2.399 |
| 21 | 365.2 | 3.111 | 2.907 |
| 25 | 436.4 | 15.88 | 4.020 |
| 29 | 92.38 | 32.08 | 3.756 |
| 33 | 111.1 | 612.2 | 3.803 |
| 37 | 32.28 | 878.2 | 4.193 |
| 41 | 384.4 | 994.0 | 4.515 |
| 45 | 33.64 | 32.91 | 3.441 |

TABLE 3

Inhibition of HIV-1 production by compounds of formula (I) in H-9 cells.

| | | RT activity (cpm) after: | | |
| --- | --- | --- | --- | --- |
| Inhibitor | Conc.- | 8 days | 12 days | 26 days |
| none | — | 198,612 | 327,570 | 239,019 |
| trans-(XXXVI) | 10 μM | 4,608 | 83,462 | 312,478 |
| trans-(XXXVI) | 50 μM | 1,319 | 758 | 1,732 |
| AZT | 20 μM | 633 | 419 | 821 |
| none | — | 64,769 | 119,580 | 227,471 |
| cis-(XXXVIII) | 20 μM | 2,618 | 130,563 | 210,583 |
| cis-(XXXVIII) | 50 μM | 1,132 | 39,752 | 231,609 |
| AZT | 20 μM | 587 | 1,316 | 679 |

The invention claimed is:

1. Cis-2-hydroxymethyl-5-(cytosin-1'-yl)-1,3-oxathiolane substantially in the form of a single enantiomer or a pharmaceutically acceptable salt thereof.

* * * * *